(12) United States Patent
Wand et al.

(10) Patent No.: US 7,195,719 B1
(45) Date of Patent: *Mar. 27, 2007

(54) HIGH POLARIZATION FERROELECTRIC LIQUID CRYSTAL COMPOSITIONS

(75) Inventors: Michael Wand, Boulder, CO (US); Xin Hua Chen, Erie, CO (US); William N. Thurmes, Longmont, CO (US)

(73) Assignee: Displaytech, Inc., Longmont, CO (US)

( * ) Notice: Subject to any disclaimer, the term of this patent is extended or adjusted under 35 U.S.C. 154(b) by 330 days.

This patent is subject to a terminal disclaimer.

(21) Appl. No.: 10/038,054

(22) Filed: Jan. 3, 2002

Related U.S. Application Data

(60) Provisional application No. 60/259,451, filed on Jan. 3, 2001.

(51) Int. Cl.
| | |
|---|---|
| C09K 19/34 | (2006.01) |
| C09K 19/30 | (2006.01) |
| C09K 19/12 | (2006.01) |
| C09K 19/20 | (2006.01) |
| C07D 303/08 | (2006.01) |

(52) U.S. Cl. .................... 252/299.61; 252/99.63; 252/299.66; 252/299.67; 544/242; 544/298; 544/335; 549/324; 549/455; 549/563

(58) Field of Classification Search ............. 428/1.1; 252/299.61, 299.5, 299.63, 299.64, 299.66, 252/299.67; 544/298, 334, 242, 335; 549/324, 549/455, 563

See application file for complete search history.

(56) References Cited

U.S. PATENT DOCUMENTS

| | | | |
|---|---|---|---|
| 4,212,762 A | 7/1980 | Dubois et al. ............... 252/299 |
| 4,367,924 A | 1/1983 | Clark et al. .................. 350/334 |
| 4,490,278 A | 12/1984 | Schubert et al. ........ 252/299.63 |
| 4,874,544 A | 10/1989 | Yong et al. ............. 252/299.61 |
| 4,886,619 A | 12/1989 | Janulis .................... 252/299.1 |
| 4,886,622 A | 12/1989 | Miyazawa et al. ...... 252/299.61 |
| 4,943,384 A | 7/1990 | Sucrow et al. ......... 252/299.61 |
| 4,952,335 A | 8/1990 | Furukawa et al. ...... 252/299.61 |
| 5,051,506 A | 9/1991 | Wand et al. .................. 544/289 |
| 5,055,221 A | 10/1991 | Scheuble et al. ....... 252/299.61 |
| 5,061,814 A | 10/1991 | Wand et al. .................. 549/560 |
| 5,062,691 A | 11/1991 | Tristani-Kendra et al. .... 359/56 |
| 5,064,566 A | 11/1991 | Hopf et al. ............. 252/299.61 |
| 5,071,589 A | 12/1991 | Dübal et al. ............ 252/299.61 |
| 5,082,587 A | 1/1992 | Janulis ................... 252/299.01 |
| 5,082,589 A | 1/1992 | Buchecker et al. ..... 252/299.63 |
| 5,110,497 A | 5/1992 | Suzuki et al. ................ 252/299 |
| 5,130,048 A | 7/1992 | Wand et al. .................. 252/299 |
| 5,138,010 A | 8/1992 | Keller et al. .................. 528/26 |
| 5,167,855 A | 12/1992 | Wand et al. ............ 252/299.01 |
| 5,168,381 A | 12/1992 | Walba .......................... 359/53 |
| 5,169,556 A | 12/1992 | Mochizuki et al. ..... 252/299.62 |
| 5,178,791 A | 1/1993 | Wand et al. ............. 252/299.65 |
| 5,178,793 A | 1/1993 | Vohra et al. ............ 252/299.61 |
| 5,180,520 A | 1/1993 | Wand et al. ............ 252/299.61 |
| 5,180,521 A | 1/1993 | Eidenschink et al. ... 252/299.61 |
| 5,190,692 A | 3/1993 | Coates et al. .......... 252/299.63 |
| 5,250,219 A | 10/1993 | Mori et al. ............. 252/299.61 |
| 5,254,747 A | 10/1993 | Janulis ....................... 568/650 |
| 5,262,082 A | 11/1993 | Janulis et al. .......... 252/299.01 |
| 5,271,864 A | 12/1993 | Wand et al. ............ 252/299.61 |
| 5,275,757 A | 1/1994 | Mineta et al. .......... 252/299.61 |
| 5,278,680 A | 1/1994 | Karasawa et al. ............ 359/40 |
| 5,286,409 A | 2/1994 | Dübal et al. ............ 252/299.61 |
| 5,322,639 A | 6/1994 | Kawabata et al. ...... 252/299.62 |
| 5,327,273 A | 7/1994 | Beresmev et al. .......... 359/104 |
| 5,338,482 A | 8/1994 | Sakaguchi et al. ..... 252/299.61 |
| 5,340,497 A | 8/1994 | Wächtler et al. ....... 252/299.61 |
| 5,340,498 A | 8/1994 | Arai et al. .............. 252/299.65 |
| 5,346,646 A | 9/1994 | Kawabata et al. ...... 252/299.62 |
| 5,346,647 A | 9/1994 | Kelly et al. ............. 252/299.63 |
| 5,348,685 A | 9/1994 | Mochizuki et al. .... 252/299.62 |
| 5,352,379 A | 10/1994 | Nishiyama et al. .... 252/299.62 |
| 5,367,391 A | 11/1994 | Johno et al. .................. 359/56 |
| 5,374,375 A | 12/1994 | Yui et al. ................ 252/299.65 |
| 5,377,033 A | 12/1994 | Radcliffe ...................... 359/75 |
| 5,378,394 A | 1/1995 | Dübal et al. ............ 252/299.61 |
| 5,378,396 A | 1/1995 | Yui et al. ................ 252/299.65 |
| 5,380,460 A | 1/1995 | Wand et al. .............. 252/299.6 |
| 5,389,287 A | 2/1995 | Nishiyama et al. .... 252/299.01 |
| 5,391,319 A | 2/1995 | Junge et al. ............ 252/299.01 |
| 5,393,458 A | 2/1995 | Kelly ..................... 252/299.01 |
| 5,399,291 A | 3/1995 | Janulis et al. .......... 252/299.01 |
| 5,399,701 A | 3/1995 | Janulis ....................... 546/298 |
| 5,417,883 A | 5/1995 | Epstein et al. ......... 252/299.01 |
| 5,422,037 A | 6/1995 | Wand et al. ............ 252/299.61 |
| 5,427,829 A | 6/1995 | Mochizuki et al. ............ 428/1 |
| 5,437,812 A | 8/1995 | Janulis et al. .......... 252/299.01 |
| 5,445,763 A | 8/1995 | Schlosser et al. ...... 252/299.61 |
| 5,453,218 A | 9/1995 | Wand et al. ............ 252/299.01 |
| 5,455,697 A | 10/1995 | Coles et al. ................. 359/103 |

(Continued)

FOREIGN PATENT DOCUMENTS

DE 3906040 9/1989

(Continued)

OTHER PUBLICATIONS

English translation by computer for JP 7-309858.*

(Continued)

*Primary Examiner*—Shean C Wu
(74) *Attorney, Agent, or Firm*—Faegre & Benson LLP

(57) ABSTRACT

The invention relates to chiral nonracemic liquid crystal compounds having achiral tails comprising a perfluoroalkyl terminal portion which are useful as components in liquid crystal to impart high polarization to the mixture. The materials of this invention can be combined with known liquid crystal host materials to impart improved properties. Chiral nonracemic compounds of this invention can function as additives or dopants in host materials to impart chirality into an LC material.

22 Claims, No Drawings

U.S. PATENT DOCUMENTS

| | | |
|---|---|---|
| 5,457,235 A | 10/1995 | Wand et al. .................. 568/65 |
| 5,474,705 A | 12/1995 | Janulis et al. ............. 252/299.1 |
| 5,482,650 A | 1/1996 | Janulis et al. ........... 252/299.01 |
| 5,498,368 A | 3/1996 | Coles .................... 252/294.67 |
| 5,529,718 A | 6/1996 | Hornung et al. ......... 252/299.61 |
| 5,534,190 A | 7/1996 | Johno et al. ............ 252/299.65 |
| 5,539,555 A | 7/1996 | Wand et al. ................. 359/100 |
| 5,543,078 A | 8/1996 | Walba et al. ........... 252/299.65 |
| 5,547,604 A | 8/1996 | Coles et al. ............ 252/299.01 |
| 5,568,299 A | 10/1996 | Yoshihara et al. ......... 359/100 |
| 5,583,682 A | 12/1996 | Kitayama et al. ........... 349/172 |
| 5,585,036 A * | 12/1996 | Wand et al. ........... 252/299.01 |
| 5,595,682 A | 1/1997 | Goodby et al. ......... 252/299.01 |
| 5,596,434 A | 1/1997 | Walba et al. ............... 349/123 |
| 5,626,792 A | 5/1997 | Wand et al. ........... 252/299.01 |
| 5,629,428 A | 5/1997 | Schlosser et al. ............ 546/303 |
| 5,637,256 A | 6/1997 | Walba et al. ........... 252/299.66 |
| 5,658,491 A | 8/1997 | Kistner et al. ......... 252/299.01 |
| 5,658,493 A | 8/1997 | Walba et al. ........... 252/299.01 |
| 5,660,762 A | 8/1997 | Ito et al. ................ 252/299.67 |
| 5,695,683 A | 12/1997 | Takeichi et al. ........ 252/299.61 |
| 5,702,637 A | 12/1997 | Johnson et al. ........ 252/299.61 |
| 5,719,653 A | 2/1998 | Minato et al. .............. 349/156 |
| 5,723,069 A | 3/1998 | Mineta et al. ......... 252/299.67 |
| 5,728,864 A | 3/1998 | Motoyama et al. ............ 560/59 |
| 5,739,885 A | 4/1998 | Mochizuki et al. ......... 349/135 |
| 5,744,060 A | 4/1998 | Tarumi et al. .......... 252/299.63 |
| 5,748,164 A | 5/1998 | Handschy et al. ............ 345/89 |
| 5,750,214 A | 5/1998 | Ito et al. ........................ 428/1 |
| 5,753,139 A | 5/1998 | Wand et al. ........... 252/299.01 |
| 5,770,108 A | 6/1998 | Totani et al. .......... 252/299.61 |
| 5,808,800 A | 9/1998 | Handschy et al. .......... 359/630 |
| 5,827,448 A | 10/1998 | Konuma et al. ........ 252/299.61 |
| 5,855,812 A | 1/1999 | Radcliffe et al. ....... 252/299.01 |
| 5,855,813 A | 1/1999 | Coles et al. ............. 252/299.5 |
| 5,856,815 A | 1/1999 | Mochizuki et al. ........... 345/97 |
| 5,858,273 A | 1/1999 | Asaoka et al. ........... 252/299.4 |
| 5,861,108 A | 1/1999 | Ishida et al. ........... 252/299.62 |
| 5,861,109 A | 1/1999 | Goodby et al. ........ 252/299.65 |
| 5,866,036 A | 2/1999 | Wand et al. ............. 252/299.6 |
| 5,888,420 A | 3/1999 | Sakai et al. ............ 252/299.01 |
| 5,922,242 A | 7/1999 | Saishu et al. .......... 252/299.62 |
| 5,928,562 A | 7/1999 | Kistner et al. ........... 252/299.6 |
| 5,932,136 A | 8/1999 | Terada et al. .......... 252/299.01 |
| 5,936,689 A | 8/1999 | Saishu et al. ................ 349/123 |
| 5,938,973 A | 8/1999 | Motoyama et al. .... 252/299.65 |
| 5,942,155 A | 8/1999 | Coles et al. ........... 252/299.64 |
| 5,943,112 A | 8/1999 | Mochizuki et al. ......... 349/173 |
| 5,949,391 A | 9/1999 | Saishu et al. .................. 345/50 |
| 5,951,914 A | 9/1999 | Matsumoto et al. ... 252/299.67 |
| 5,968,413 A | 10/1999 | Mine et al. ............ 252/299.65 |
| 5,972,241 A | 10/1999 | Johnson et al. ........ 252/299.61 |
| 5,972,243 A | 10/1999 | Mine et al. ............ 252/299.65 |
| 5,976,409 A | 11/1999 | Mineta et al. ......... 252/299.65 |
| 5,980,780 A | 11/1999 | Motoyama et al. .... 252/299.64 |
| 5,985,172 A | 11/1999 | Motoyama et al. .... 252/299.64 |
| 6,001,278 A | 12/1999 | Matsumoto et al. ... 252/299.65 |
| 6,002,042 A | 12/1999 | Mine et al. .................... 560/66 |
| 6,007,737 A | 12/1999 | Nishiyama et al. .... 252/299.01 |
| 6,018,070 A | 1/2000 | Ito et al. ........................ 560/76 |
| 6,019,911 A | 2/2000 | Hirano et al. .......... 252/299.62 |
| 6,045,720 A | 4/2000 | Shundo et al. ......... 252/299.61 |
| 6,051,639 A | 4/2000 | Mehl et al. .................. 524/205 |
| 6,057,006 A | 5/2000 | Kirsch et al. ................... 428/1 |
| 6,057,007 A | 5/2000 | Amano et al. .................. 428/1 |
| 6,084,649 A | 7/2000 | Amano et al. ................ 349/96 |
| 6,106,908 A | 8/2000 | Duffy et al. ................. 428/1.1 |
| 6,139,771 A | 10/2000 | Walba et al. ........... 252/299.01 |
| 6,413,448 B1 | 7/2002 | Wand et al. ........... 252/299.63 |
| 6,838,128 B1 * | 1/2005 | Wand et al. ................. 428/1.1 |
| 2002/0195585 A1 * | 12/2002 | Gough et al. .......... 252/299.61 |

FOREIGN PATENT DOCUMENTS

| | | |
|---|---|---|
| DE | 3928267 | 2/1991 |
| DE | 4315867 | 11/1994 |
| EP | 0 307 880 | 3/1989 |
| EP | 0 331 091 | 9/1989 |
| EP | 0 356 672 | 3/1990 |
| EP | 0 401 522 | 12/1990 |
| EP | 405868 A2 | 1/1991 |
| EP | 255236 B1 | 5/1994 |
| EP | 0 545 409 B1 | 3/1996 |
| EP | 425304 B1 | 7/1996 |
| EP | 579545 B1 | 3/1997 |
| EP | 0 769 543 A1 | 4/1997 |
| EP | 736078 B1 | 6/1998 |
| JP | 1213390 A2 | 8/1989 |
| JP | 63039286 | 8/1989 |
| JP | 01041845 | 12/1989 |
| JP | 01053791 | 12/1989 |
| JP | 01071776 | 12/1989 |
| JP | 1316339 A2 | 12/1989 |
| JP | 1316367 A2 | 12/1989 |
| JP | 1316372 A2 | 12/1989 |
| JP | 7-309858 * | 11/1995 |
| JP | 8-82778 A | 3/1996 |
| JP | 8-113784 | 5/1996 |
| JP | 228128 A | 8/2000 |
| WO | 86/06401 | 11/1986 |
| WO | 87/05015 | 8/1987 |
| WO | 87/05018 | 8/1987 |
| WO | WO 89/10356 | 11/1989 |
| WO | WO 91/00897 | 1/1991 |
| WO | WO 97/36908 | 10/1997 |
| WO | WO 99/33814 | 7/1999 |
| WO | WO 00/31210 | 6/2000 |

OTHER PUBLICATIONS

Arnett, K.E. et al., "Technique For Measuring Electronic-Based Electro-Optic Coefficients of Ferroelectric Liquid Crystals" (1995), *Mat. Res. Soc. Symp. Proc.* 392:135-146.

Bezborodov, V.S. et al., "Synthesis, mesomorphic properties and potential applications of aryl esters of 4-n-alkycyclohexene-1-carboxylic acids in electrooptic displays," (1989) CAPLUS 1989:240081 (abstract only).

Bezborodov et al. (1989), "Synthesis, mesomorphic properties and potential applications of aryl esters of 4-n-alkycyclohexene-1-carboxylic acids in electrooptic displays," *Liq. Cryst.* 4(2):209-215.

Blinov L.M. and Tournilhac, F., "Infra-Red Dichroism of Mesophases Formed By Polyphilic Molecules. 1. Development of the Technique and Study of Compounds With One Long Perfluorinated Tail"(1993), *Molecular Materials* 3:93-111.

Booth, C.J. et al., "The ferro-,ferri- and antiferro-electric properties of a series of novel 2- or 3-substituted-alkyl 4-(4'-dodecyloxybiphenyl-4-carbonyloxy)-benzoate esters" (1996), *Liquid Crystals* 20(6):815-823.

Booth, C.J. et al., "Achiral swallow-tailed materials with 'antiferroelectric-like' structure and their potential use in antiferroelectric mixtures" (1996), *Liquid Crystals* 20(4):387-392.

CAPLUS 1998: 624749.

CAPLUS 2001: 305417.

Chandani, A.D.L. et al., "Novel Phases Exhibiting Tristable Switching" (Jul. 1989), *Jpn. J. App. Phys.* 28:L1261-1264.

Chandani, A.D.L. et al., "Antiferroelectric Chiral Smectic Phases Responsible for the Tristable Switching in MHPOBC"(Jul. 1989), *Jpn. J. App. Phys.* 28:L1265-1268.

Chandani, A.D.L. et al., "Tristable Switching in Surface Stabilized Ferroelectric Liquid Crystals with a Large Spontaneous Polarization" (May 1988), *Jpn. J. App. Phys.* 27(5):L729-L732.

Clark, N.A. and Lagerwall, S.T., "Submicrosecond bistable electrooptic switching in liquid crystals"(Jun. 1980), *Appl. Phys. Lett.* 36:899-901.

Clark, N.A. et al., Electro-Optic Characteristics of de Vries Tilted and Smectic Liquid Crystals: Analog Behavior in the Smectic A* and Smectic C* Phases (2002) *Appl. Phys. Lett.* 80:4097-99.

Coates, D. and Greenfield, S. (1991), "Liquid crystal compositions comprising 4-alkyl-4'-(o-fluorophenethyl)bicyclohexanes for supertwisted nematic electrooptical display devices," Chem. Abstracts, vol. 115, Abstract No. 115: 82430v, p. 752.

Dawson, D.J. et al., (1987) "Cocyclotrimerization of Aryl Acetylenes: Substituent Effects on Reaction Rate" *Am. Chem. Soc. Sym.* 346 Ch 38:446-456.

de Vries, A., "Experimental Evidence Concerning Two Different Kinds Of Smectic C To Smectic A Transitions" (1977), *Mol. Cryst. Liq. Cryst. (Letters)* 41:27-31.

de Vries, A., "The Implications of the Diffuse-Cone Model for Smectic A and C Phases and A-C Phase Transitions" (1979), *Mol. Cryst. Liq. Cryst. (Letters).* 49:179-185.

Drzewinski, W. et al. "Antiferroelectric Liquid Crystals with Fluorinated Parts of Terminal Chains" CAPLUS 1998:624787 (abstract only).

Edgar, K. J. and Falling, S.N., "An Efficient and Selective Method for the Preparation of Iodophenols" (1990) *Org. Chem.* 55:5287-5291.

Escher, C. et al. (1991), "Liquid crystal compositions for electrooptical display devices," Chem. Abstracts vol. 115, Abstract No. 115:194312q, p. 775.

Fleming, F. F. and Jiang, T., "Unsaturated Nitriles: Optimized Coupling of the Chloroprene Grignard Reagent[1] with ω-Bromonitriles" *J.Org. Chem.* (1997) 62:7890-7891.

Fung, B.M. et al. (1989), "Liquid crystals containing a cyclohexene ring," *Mol. Cryst. Liq. Cryst. Lett.* 6(6): 191-196.

Gorecka, E. et al., "Molecular Orientational Structures in Ferroelectric, Ferrielectric and Antiferroelectric Smectic Liquid Crystal Phases as Studied by Conoscope Observation" (Jan. 1990), *Jap. J. Appl. Phys.* 29(1):131-137.

Hartmann, W., "Uniform SSFLC Director Pattern Switching" (1988), *Ferroelectrics* 85:67-77.

Heinemann, S. et al., "Synthesis and Dielectric Investigations of New Swallow-Tailed Monomers and Polymers" (1993), *Mol. Cryst. Liq. Cryst.* 237:277-283.

Heinemann, S. et al., "Competition between dipolar and steric interactions in swallow-tailed compounds" (1993), *Liquid Crystals* 13(3):373-380.

Hide, F. et al., "Dynamic Polarized Infrared Spectroscopy of Electric Field-Induced Molecular reorientation in a Chiral Smectic-A Liquid Crystal" (Sep. 1995), *Phys. Rev. Lett.* 75(12):2344-2347.

Inui, S. et al., "Thresholdless antiferroelectricity in liquid crystals and its application to displays"(1996), *J. Mater. Chem.* 6(4):671-673.

Inukai, T. et al., "Dicyanohydroquinone cyclohexanecarboxylic acid esters," (1980) CAPLUS 1989:604304 (abstract only).

Johno, M. et al., "Correspondence between Smectic Layer Switching and DC Hysteresis of Apparent Tilt Angle in an Antiferroelectric Liquid Crystal Mixture" (Jan. 1990), *Jap. J. Applied Phys.* 29(1):L111-114.

Johno, M. et al., "Smectic Layer Switching by an Electric Field in Ferroelectric Liquid Crystals Cells" (Jan. 1989), *Jpn. J. App. Phys.* 28(1):L119-120.

Kagawa, A. et al., "Fast Response Time STN=LCD with High Contrast Ratio" (1995), Proceedings of the 15th International Display Research Conference 177-180.

Kelly, S.M. (1991), "Four unit linking groups. II. Some novel smectic C materials," *Liq. Cryst.* 10(2):243-260.

Klopper et al., "IR-Modulation Spectroscopy on the Collective Dynamics of Free-Standing Ferroelectric Liquid Crystalline Films" (Jan. 1997), J. Physique II France 7(1):57-67.

Li et al. (1991) "Liquid crystals with a chiral core: cyclohexene carboxylates," *Mol. Cryst. Liq. Cryst.* 199:379-386.

Matsumoto, T. et al., "A novel property caused by frustration between ferroelectricity and antiferroelectricity and its application to liquid crystal displays—frustoelectricity and V-shaped switching" (Sep. 1999) *J. Mater. Chem.* 9:2051-2080.

McMullen, W. et al., "Theoretical Studies of the Isotropic-Nematic Interface" *Mol. Cryst. Liq. Cryst.*(1991) 198:107-117.

Mikami, K. et al., "Diastereotropic Phenomena for the Appearance of SmCA*Phase in α-Trifluoromethyl-β-methyl-substituted Liquid Crystalline Molecules" (1996) *Chemistry Letters.*

Mikami, K. et al., "Binaphthol-Titanium Complex-Catalyzed Fluoral-Ene Reaction with Vinyl Sulfides for Asymmetric Synthesis of Diastereomeric α-Trifluoromethyl-β-methyl Carbinols: Diastereomer Switch of Antiferroelectric or Ferroelectric Properties of Diastereomeric Liquid-Crystalline Systems[1]" (Sep. 1996) *SYNLETT* 837-838.

Mochizuki, A. et al., "A High Contrast and High Transmittance Multiplexing SSFLC Display Utilizing Naphthalene Base Crystal Materials" (1991), *Ferroelectrics* 122:37-51.

Mochizuki, A. et al., "Zigzag defect free alignment and good bistability of surface stabilized $S_c$ * Cells" (1991), *Ferroelectrics* 113:353-359.

Mottram, N.J. and Elston, S.J., "Preliminary communication Thresholdless switching induced by polar anchoring in antiferroelectric liquid crystals" (1999) *Liquid Crystals* 26(12):1853-1856.

Nakagawa, A., A Hysteresis Model for Antiferroelectric $SmC_{A^*}$ (Aug. 1991), *Jap. J. App. Phys.* 30(8):1759-1764.

Nohira, H. et al. (1989), "Optically active compounds and liquid-crystal compositions and devices containing them," Chem. Abstracts vol. 111, Abstract No. 111:15479x, p. 571.

Ostrovskii, B.I. et al., "Evidence of Tilted Dimeric Mesophase for Terminally Polar Polyphilic Mesogens" (1995), *J. Physique II France* 5(7):979-1001.

Park, B. et al., "Molecular motion in a smectic liquid crystal showing V-shaped switching as studied by optical second-harmonic generation" (Apr. 1999)*Physical Review E* 59(4) 3815-3818.

Perova, T.S. et al., "Study Of The Molecular Orientation In A Chiral Smectic Liquid Crystal Mixture using Infrared Dichroism" (1996), *Ferroelectrics* 180(1-4):105-115.

Redmond, M. et al., "Ferroelectric and Electroclinic Characterization of a New Organic Siloxane Bimesogen." (1993) *Ferroelectrics* 148:323-336.

Rieker, T.P. et al., "'Chevron' Local Layer Structure in Surface-Stabilized Ferroelectric Smectic-C Cells" (Dec. 1987), *Physical Rev. Letts.* 59(23):2658-2661.

Rudquist, J.P. et al., "The case of thresholdless antiferroelectricity: polarization-stabilized twisted SmC* liquid crystals give V-shaped electro-optic response" (1999), *J. Mater. Chem.* 9:1257-1261.

Sakaigawa, A. and Nohira, H., "Properties of Ferroelectric Liquid Crystal Mixtures Containing Fluorine Substituted Compounds"(1993) *Ferroelectrics* 148:71-78.

Schmitt, K. et al., "Strongly non-linear optical ferroelectric liquid crystals for frequency doubling" (1993) *Liquid Crystals* 14(6) 1735-1752.

Seomun, S.S. et al., "Evolution of Switching Characteristics from Tristable to V-Shaped in an Apparently Antiferroelectric Liquid Crystal" (Jun. 1997), *J. Appl. Phys.* 36:3586-3590.

Shibata, T. et al., "Liquid Crystal Composition," (1996) CAPLUS 1997:179123 (abstract only).

Takanishi, Y. et al., "Spontaneous Formation of Quasi-Bookshelf Layer Structure in New Ferroelectric Liquid Crystals Derived from a Naphthalene Ring" (Jun. 1990), *Jap. J. Applied Phys.* 29(6):L984-L986.

Takatsu, H. et al. (1984), "Synthesis and Some Properties of Nematic Compounds Containing Three Ring Systems," *Mol. Cryst. Liq. Cryst.* 111:311-319.

Takehara, S. et al. (1991), "A ferroelectric chiral smectic liquid crystal composition containing a high temperature liquid crystal: trans-1-(hetero)aryloxymethyl-4-alkylcyclohexane," Chem. Abstracts, vol. 115, Abstract No. 115: 102976h, p. 735.

Takehara, S. et al. (1991), "Ferroelectric liquid crystal compositions," Chem. Abstracts, vol. 115, Abstract No. 115:82385j, p. 750.

Takiguchi, T. et al. (1991), "Ferroelectric liquid crystal composition," Chem. Abstracts, vol. 115, Abstract No. 115:82387m, p. 750.

Tuffin, R. P. et al., "Non-Chiral Compounds Exhibiting Alternating Tilt Smectic Phases" (1995) *Mol. Cryst. Liq. Cryst.* 260:51-67.

Zhuang, Z., "Interfacial Interactions, Director Configurations and Layer Structures of Surface Stabilized Ferroelectric Liquid Crystals" (1991), *Ph.D. Thesis, University of Colorado*, Boulder CO. 105 pages.

US 6,030,547, 02/2000, Hasegawa et al. (withdrawn)

* cited by examiner

HIGH POLARIZATION FERROELECTRIC LIQUID CRYSTAL COMPOSITIONS

This application claims priority to U.S. Provisional Application 60/259,451, filed Jan. 3, 2001, which is incorporated by reference in its entirety to the extent not inconsistent with the disclosure herewith.

BACKGROUND OF THE INVENTION

The present invention relates generally liquid crystal compounds and compositions and to optical devices employing liquid crystal compositions in optical switching and display elements. The invention more specifically relates to chiral nonracemic compounds useful as dopants in ferroelectric liquid crystal compositions to impart high polarization and fast switching speed. The dopants combine a rod-like mesogenic core with a chiral nonracemic tail and an achiral tail that comprises a perfluoroalkyl terminal portion.

The present invention relates to compounds useful as components in liquid crystal (LC) compositions, particularly as components of LC compositions that exhibit smectic phases and more particularly as components of LC compositions that exhibit smectic A and/or smectic C phases. LC compositions of this invention may also exhibit nematic phases. LC compositions of this invention can be ferroelectric liquid crystals (FLCs). The invention also relates to optical devices employing LC and FLC compositions of the invention in optical switching and display elements.

Several types of smectic liquid crystal materials (LCs) have been investigated for rapid switching, view-angle enhancement and higher contrast, including surface-stabilized ferroelectric LCs (FLCs), deformed helix ferroelectric LCs (DHFLCs), and antiferroelectric LCs (AFLCs). Recently, smectic material exhibiting thresholdless or more properly V-shaped switching LCs (VLCs) have been described (Inui, S. et al. (1996) J. Mater. Chem. 6(4): 671–673; Seomun, S. S. et al. (1997) Jpn. J. Appl. Phys. 36:3580–3590).

Liquid crystal (LC) compositions exhibit one or more LC phases. LC compositions may be composed of one or more components. Components of LC compositions may exhibit liquid crystal phases, have latent liquid crystal phases or be compatible with (not suppress) liquid crystal phases in the LC composition. LC compounds and components of LC mixtures of this invention are rod-like molecules most typically having a generally linear mesogenic core with one or more directly or indirectly linked alicyclic or aromatic rings (which may be fused aromatic rings) and linear or branched tail groups distributed on either side of the mesogenic core, e.g.:

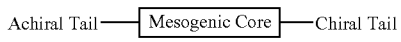

LC components which do not themselves exhibit liquid crystal phases, but which exhibit LC phases on combination with one or more other components are described as having "latent" liquid crystal phases. Chiral nonracemic LCs useful in FLC, DHFLC, AFLC and VLC compositions have at least one component that has a chiral nonracemic tail group. FLC, DHFLC, AFLC and VLC compositions may be composed entirely of chiral non-racemic components, but are typically composed of a mixture of chiral nonracemic and achiral or racemic components.

Ferroelectric LCs when aligned parallel to the substrate surfaces using the surface stabilized effect (in an surface-stabilized ferroelectric liquid crystal (SSFLC) device) exhibit two stable state switching on a microsecond time scale. Antiferroelectric LCs exhibit three stable-state switching, which by application of a bias field can be converted for use in a bistable switching mode LC devices. Two of the AFLC states have the same transmittance, so that alternate symmetrical switching can be used in AFLC devices. VLCs, in contrast, exhibit very rapid, analog electro-optic response, allow symmetrical driving, and no dc balance is required. VLCs are particularly attractive for applications requiring generation of multiple levels of gray scale.

SUMMARY OF THE INVENTION

The invention relates to chiral nonracemic liquid crystal compounds having achiral tails comprising a perfluoroalkyl terminal portion which are useful as components in liquid crystal to impart high polarization to the mixture. The materials of this invention can be combined with known liquid crystal host materials to impart improved properties. Chiral nonracemic compounds of this invention can function as additives or dopants in host materials to impart chirality into an LC material.

Most generally the invention provides a method for increasing the polarization of a given FLC mixture containing a chiral nonracemic dopant by replacing the achiral tail of the chiral nonracemic dopant with an achiral tail that comprises a terminal perfluoroalkyl portion, such as an achiral tail of formula:

where Y is oxygen or a single bond and n and m are integers ranging from 1 to 20. The sum n+m is preferably 5–12. In specific embodiments n is 1, 2, 3, 4, 5, or 6 and m is 2 to 10. The enhancement of spontaneous polarization of LC mixtures containing one or more compounds of this invention is general an will apply with a variety of chiral nonracemic tail groups.

More specifically the invention relates to chiral nonracemic compounds of general formula:

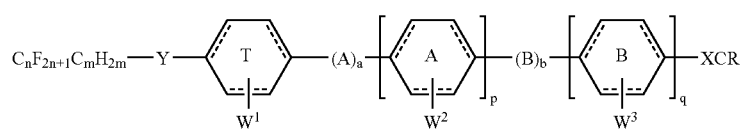

wherein n and m are integers ranging from 1 to about 20;
a, b, p and q are either 0 or 1, when p is 0, a is 0 and when q is 0, b is 0;
Y is a single bond or an oxygen;
X is selected from the group consisting of a single bond, oxygen, —CO—, —O—CO—, and —CO—O—;
CR is a chiral, non-racemic tail group;
A and B, independently, are linker groups that can be selected from the group consisting of —CO—, —O—CO—, —CO—O—, —CH$_2$—CH$_2$—, —CH$_2$—CH$_2$—O—, —O—CH$_2$—CH$_2$—, —C≡C—, —C=C—, or —C=C—C=C—;
W$^1$, W$^2$, and W$^3$, independently, represent one or more optional substituents on core rings which can be selected from the group consisting of H, halide, alkyl, alkoxy, haloalkyl, alkenyl, haloalkenyl, nitro, or nitrile; and
rings T, A and B together representing the mesogenic core are selected from the group of aromatic or alicyclic rings, with preferred rings being cyclohexane, cyclohexene, a phenyl, pyridine, pyrimidine or a naphthyl group, wherein one or two ring CH$_2$ groups or CH groups are replaced by —N—, S, NH, —O— or —C=O.

In a specific embodiment CR is not a chiral hydrocarbon tail;

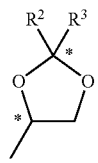
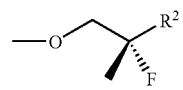

as well as —CH$_2$—(C*HF)$_f$—R$^2$ wherein * indicates an asymmetric carbon; f is 1, 2, or 3, R$^1$ and R$^3$, independently of each other, are lower alkyl or alkenyl groups [lower alkyl having 1 to 6 carbon atoms] which are optionally substituted with one or more halogens, e.g., perfluoralkyl groups, and R$^2$ is an alkyl, alkenyl, ether, thioether, silyl group having from 1 to about 20 carbon atoms wherein one or more CH$_2$ groups are replaced with —S—, —O—, —CO—, —CO—O—, —O—CO—, or —Si(R')$_2$, and where R' is a lower alkyl optionally substituted with one or more halogens. Preferred lower alkyl groups are methyl groups.

Mesogenic cores of this invention include those of Scheme 1.

Specific compounds of this invention include:

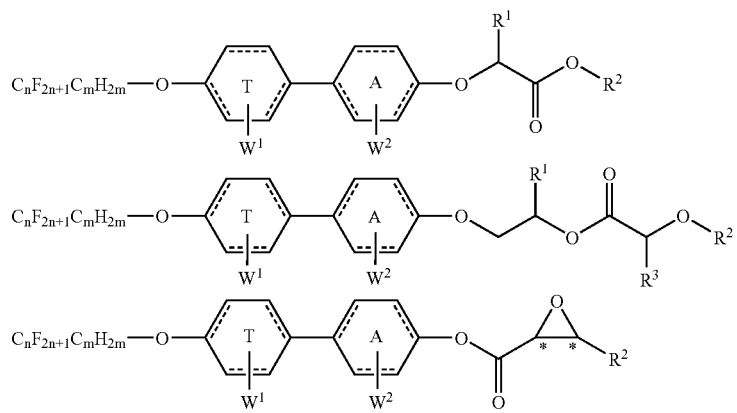

Specific chiral tails of this invention include, among others,

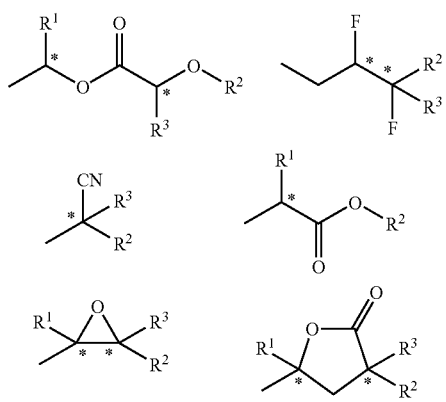

where variable are defined above and * indicates an asymmetric carbon.

FLC compositions of this invention include those that comprise 1 to 100% of one or more chiral nonracemic compound of this invention. Preferred compositions comprise 1 to 50% of one or more chiral nonracemic compounds of this invention. More preferred compositions comprise 1 to 25% of one or more chiral nonracemic compounds of this invention. Compositions of this invention also include those which comprise one or more chiral nonracemic compounds of this invention present in the composition at a level of 10% or less. FLC compositions of this invention include those which exhibit Ps of 10 nC/cm$^2$ or more, as measured by conventional methods. In particular, FLC compositions include those which exhibit Ps of 25 nC/cm$^2$ or more. Preferred FLC compositions exhibit Ps of 10 nC/cm$^2$ or more or Ps of 25 nC/cm$^2$ or more when contain 10 weight % or less (total amount) of one or more compounds of this invention. Ps is typically measured at room temperature.

Specific compounds of this invention with Ps data are provided in Table 1.

The following examples illustrate methods for synthesis of chiral nonracemic compounds of this invention. The synthesis of perfluorinated alcohols and core moieties with chiral nonracemic tails are illustrated. These materials are readily coupled to provide the compounds of this invention.

Schemes 2 and 3 illustrates a number of compounds that can be combined with the chiral nonracemic compounds of this invention to provided useful mixtures. Compounds illustrated therein can be prepared by methods that are well known in the art from readily available starting materials. Methods that are useful in the preparation of various LC compounds and FLC compounds are provided, for example in U.S. Pat. Nos. 5,051,506; 5,061,814; 5,130,048; 5,167, 855; 5,178,791; 5,178,793; 5,180,520; 5,271,864; 5,278, 680; 5,380,460; 5,422,037; 5,453,218; 5,457,235; 5,539, 555; 5,543,078; 5,585,036; 5,626,792; 5,637,256; 5,658, 493; 5,753,139; 5,866,036; and 6,139,771. Each of which is incorporated by reference herein for synthetic methods applicable to the synthesis of compounds of this invention including compounds of structures 1–16 in Scheme 2. The listed patents along with U.S. Pat. Nos. 5,168,381 and 5,596,434 also provide detail of how LC and FLC compositions of this invention can be applied for the production of LC cells and optical devices.

Concurrently filed U.S. patent applications Ser. No. 09/754,034 (now U.S. Pat. No. 6,759,101), Ser. No. 09/753, 749 (now abandoned) and Ser. No. 09/754,033 (now U.S. Pat. No. 6,782,812) all provide description of LC components and methods of synthesis of those components that can be combined with the chiral nonracemic compounds of this invention to provide useful FLC compositions.

In addition, chiral racemic compounds or corresponding achiral compounds of this invention can be employed as additional compatible components of FLC compositions of this invention.

LC and FLCS compositions of this invention are useful in the preparation of optical devices, particularly for optical switching devices and displays. Of particular interest are SSFLC devices for use for rapid optical switching as in display applications. Those of ordinary skill in the art understand how to make LC and FLCS cells and devices that utilize the compositions of this invention. Various methods and techniques for constructing LC and FLCS cells and for use of such cells are known in the art and can be readily adapted for use with compositions of this invention. The compositions of this invention are particularly well suited for providing devices that can operate (in a smectic C phase, for example) over a broad temperature range.

All references cited herein are incorporated by reference herein to the extent that they are not inconsistent with the disclosure herein.

SCHEME 1

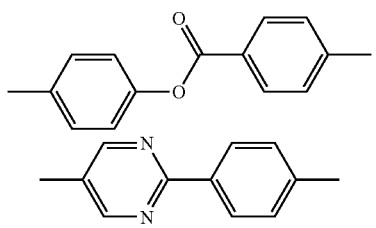

-continued

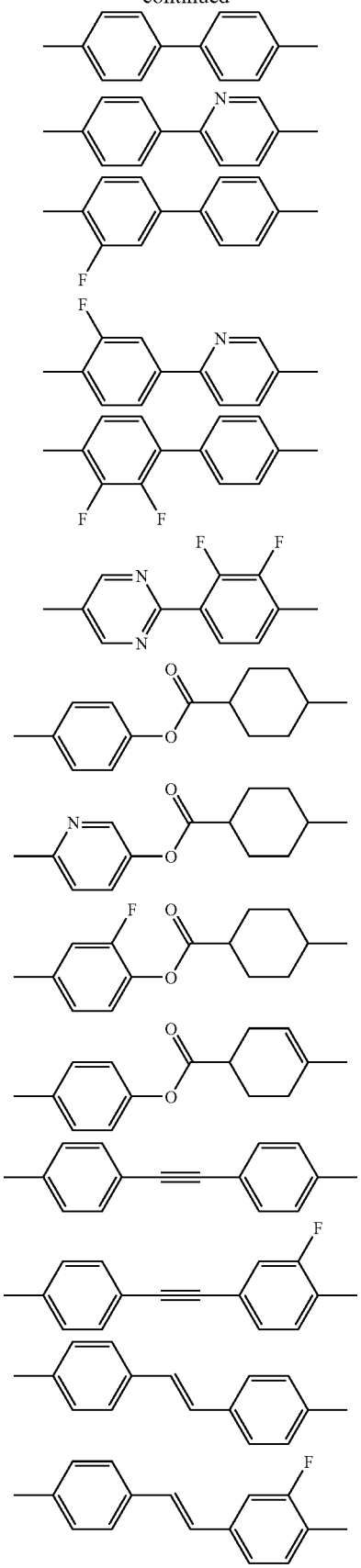

-continued
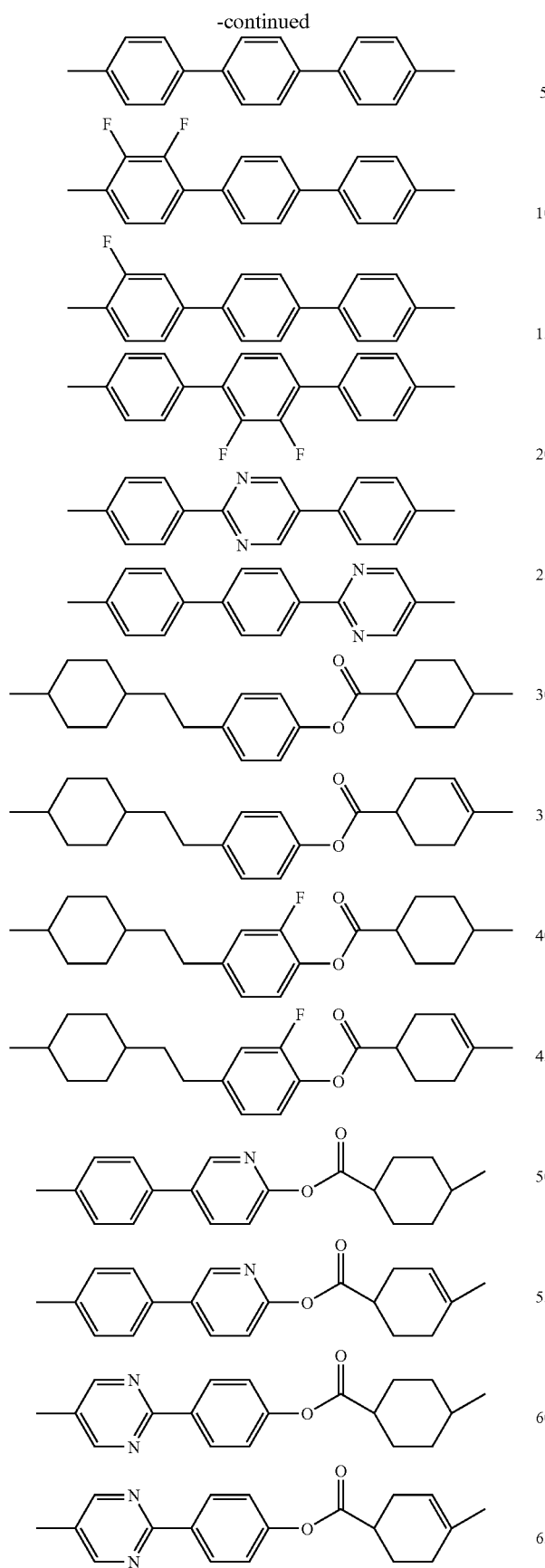
-continued
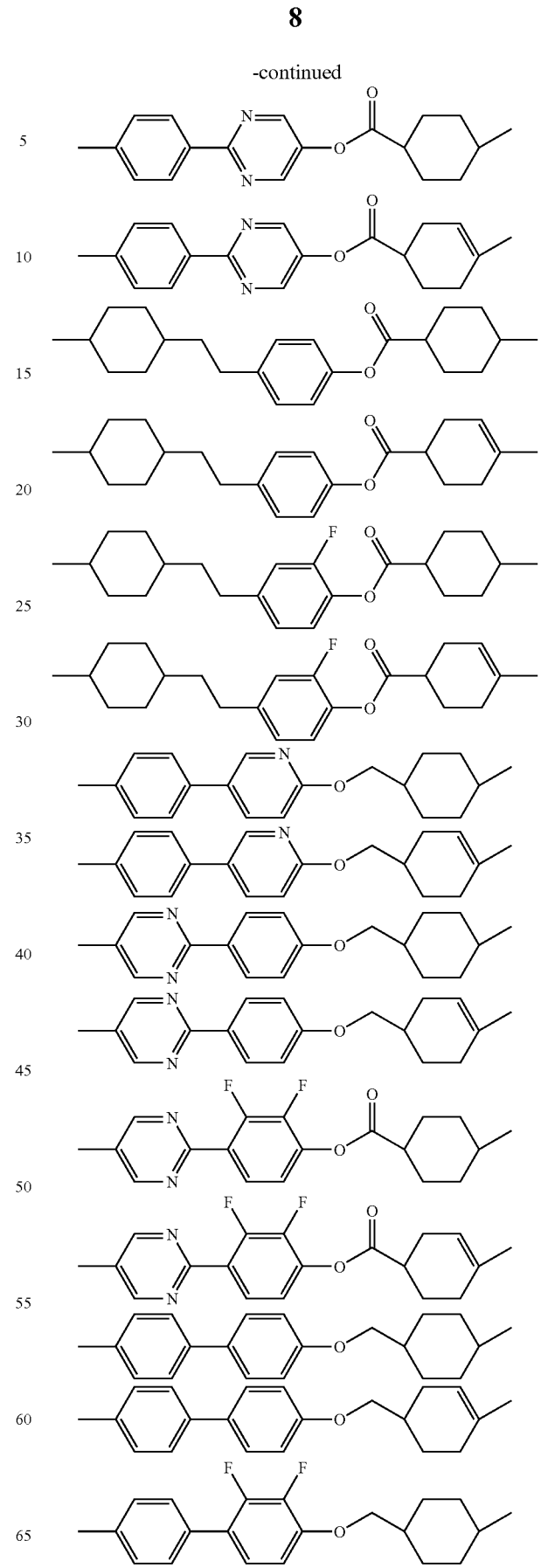

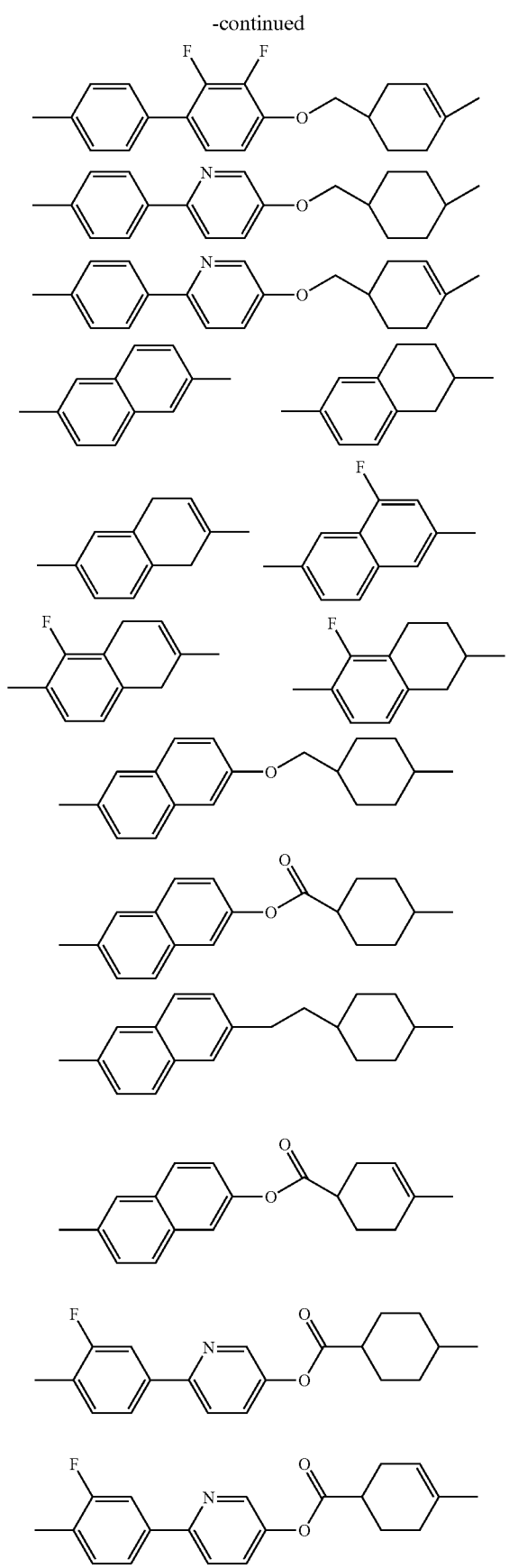
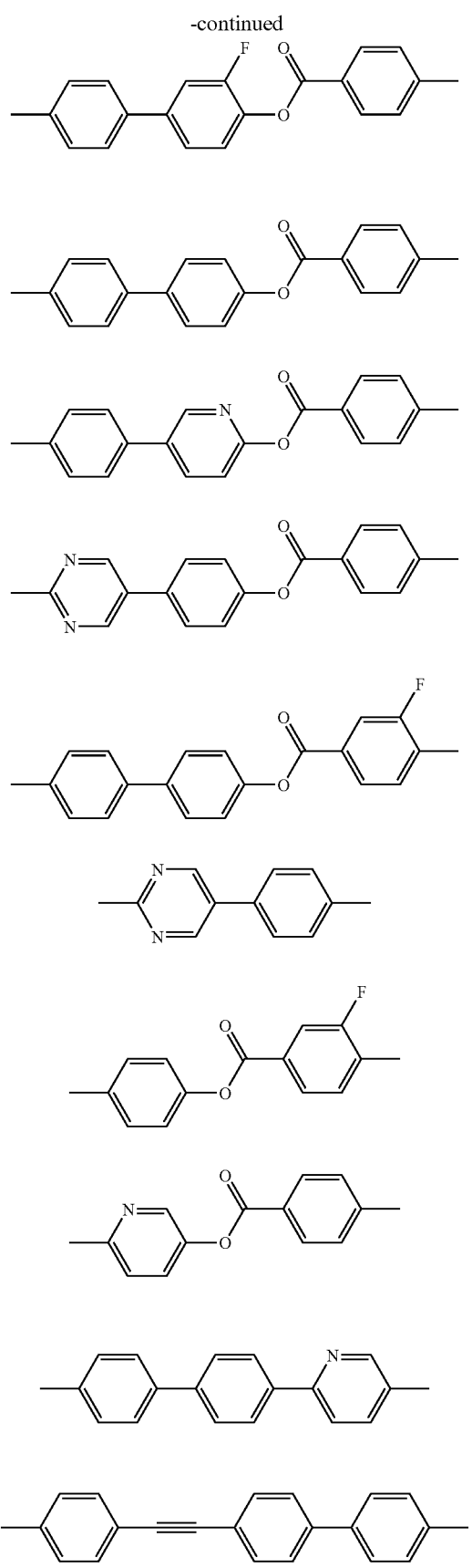

SCHEME 2
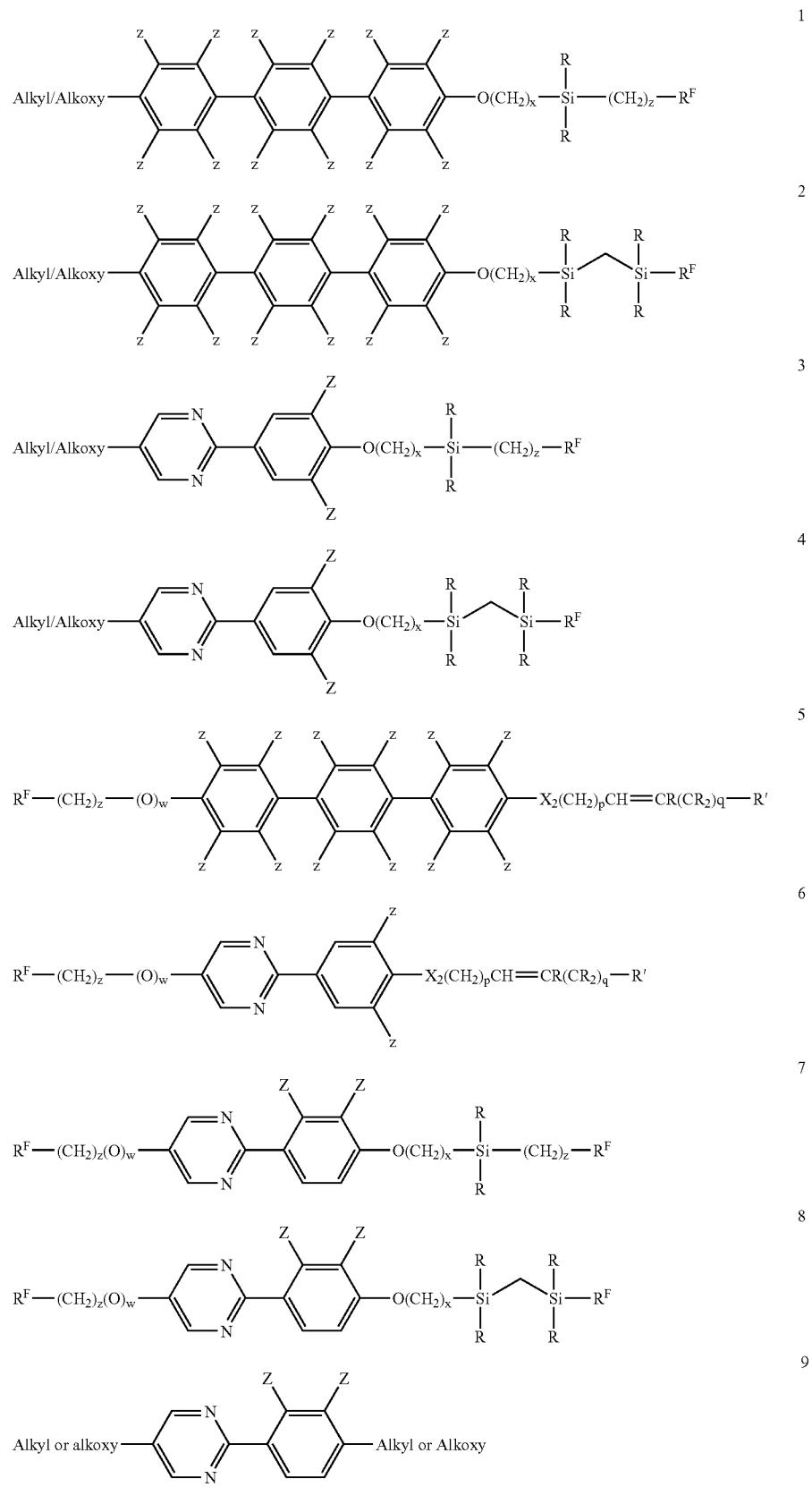

-continued

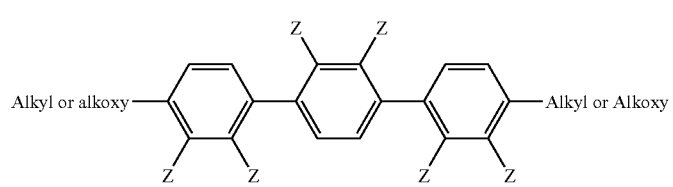
10

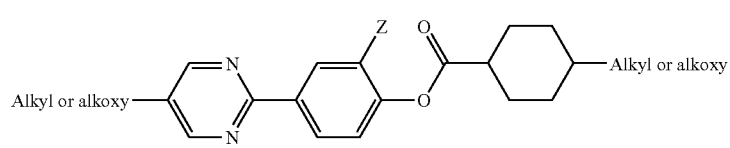
11

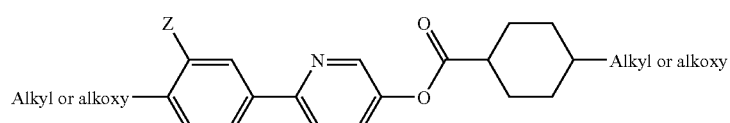
12

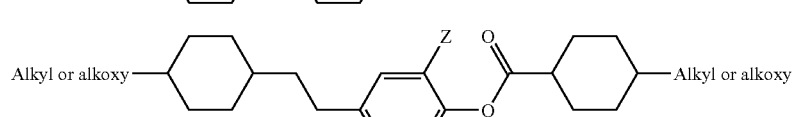
13

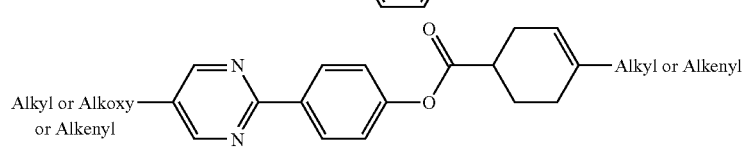
14

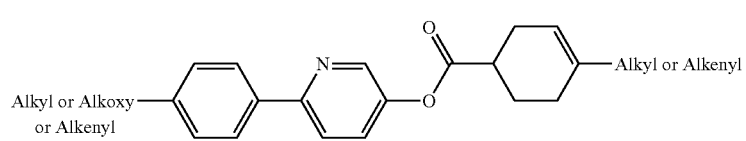
15

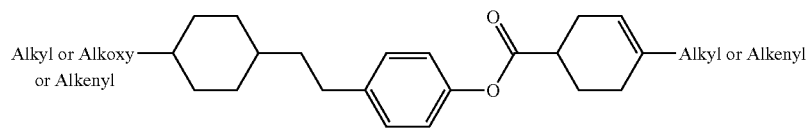
16 wherein p, x and z are integers ranging from 1 to 20, inclusive, q is 0 or an integer ranging from 1 to 20, inclusive; w is 0 or 1; R are alkyl groups, preferably having from 1 to 6 carbon atoms; R' is an alkyl group having from 5 to 20 carbon atoms; $R^F$ is a perfluoroalkyl group; Z is H or a F; and alkyl or alkoxy groups are those that have 1 to 20 carbon atoms.

SCHEME 3

| MDW # | Structure | Phase Diagram |
|---|---|---|
| 950 | 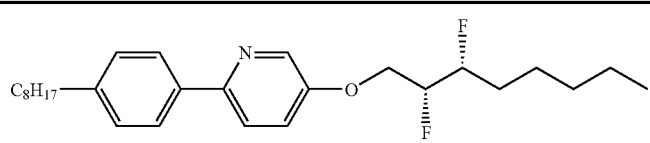 | X<-90-I-94-> |
| 987 | 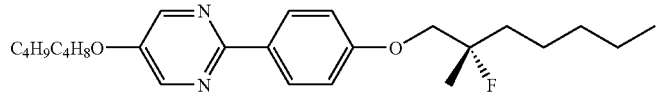 | X<----21------ SmC*<-54-SmA<-63-I-53-> S?-57-> |

-continued
SCHEME 3
| | | |
|---|---|---|
| 644 | 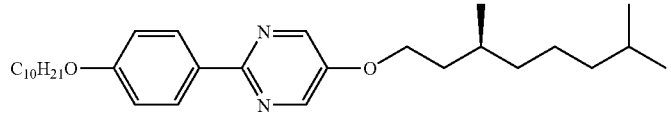 | X<-20-N<-41-I-43>  -47-> |
| 699 | 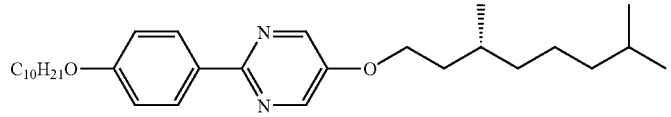 | |
| 139 | 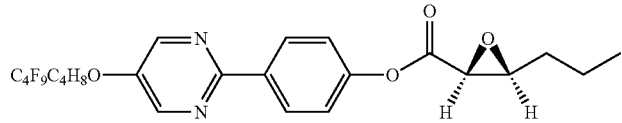 | X-75->I<-86- |
| 337 | 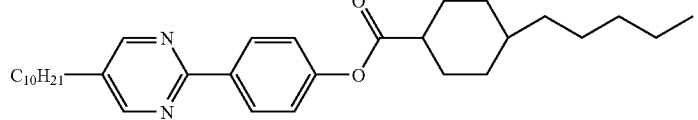 | X<-100-C<-105-N<-169-I |
| 1135 | 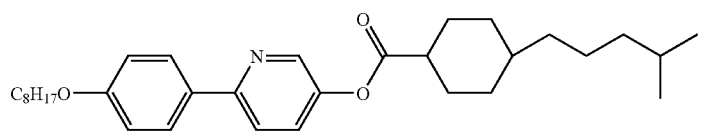 | X<-73.5-S?<-85-C<-104-A<-175-N<-186-I |
| 1638 | 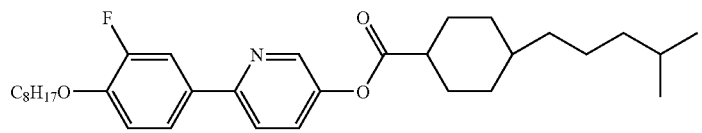 | |
| 1458 | 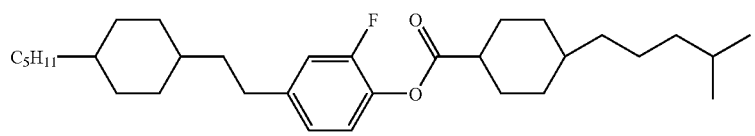 | |
| 1671 | 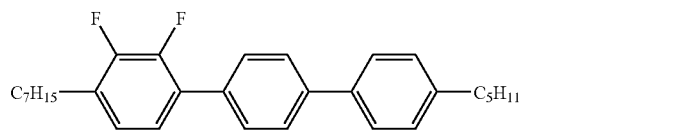 | X-56->C-106->A-131->N-136->I |
| 1673 | 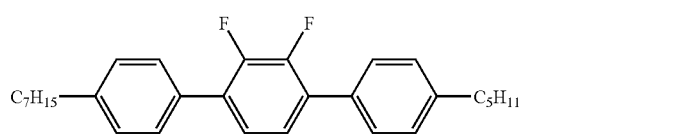 | X-37->N-112->I<br>X<-24-C |
| 1674 | 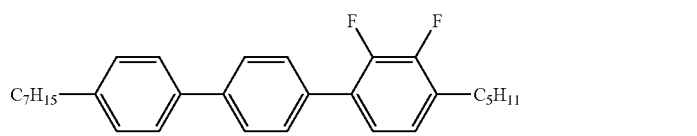 | X-66->SI-75->C-119->A-135->N-137->I |
| 31 | 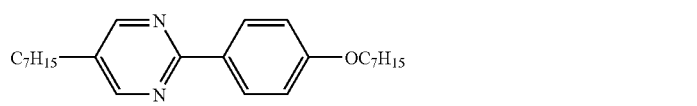 | |

| | -continued | |
|---|---|---|
| | SCHEME 3 | |
| 3 | C₇H₁₅—[pyrimidine]—[phenyl]—OC₈H₁₇ | X-49->A-44->N-69.5->I |
| 1695 | C₈H₁₇—[pyrimidine]—[phenyl]—OC₆H₁₃ | |
| 5 | C₈H₁₇—[pyrimidine]—[phenyl]—OC₁₂H₂₅ | X-43.2->C-62.4->A-66.8->N-68.2->I |
| 4 | C₉H₁₉—[pyrimidine]—[phenyl]—OC₈H₁₇ | X-33->C-60->A-74.5->I |
| 913 | C₉H₁₉—[pyrimidine]—[difluorophenyl]—OC₇H₁₅ | X-43->C-50->I<-44-<52- |
| 911 | C₉H₁₉—[pyrimidine]—[difluorophenyl]—OC₉H₁₉ | X-44->C-52->I<-37-<-52- |
| 374 | C₈H₁₇O—[pyrimidine]—[phenyl]—OC₆H₁₃ | |
| 1054 | C₈H₁₇O—[phenyl]—[pyridine]—O-C(=O)—[cyclohexene]—CH₂CH₂CH=C(CH₃)₂ | X<----- C<-135-N<-150-I-55->Sx-82-> |
| 942 | C₅H₁₁—[cyclohexyl]—CH₂CH₂—[phenyl]—O-C(=O)—[cyclohexene]—CH₂CH₂CH=C(CH₃)₂ | |
| 576 | C₁₀H₂₁—[pyrimidine]—[phenyl]—O-C(=O)—[cyclohexene]—CH₃ | X<-35-X?<-45-C<-68-N<-107-I -50->-54-> |
| 1059 | C₁₀H₂₁—[pyrimidine]—[phenyl]—O-C(=O)—[cyclohexene]—CH₂CH₂CH(CH₃)₂ | |
| 336 | C₁₀H₂₁—[pyridine]—[phenyl]—O-C(=O)—[cyclohexene]—CH₂CH₂CH=C(CH₃)₂ | X<-27-C<-83-N<-106-I-40-> |

-continued
SCHEME 3
577
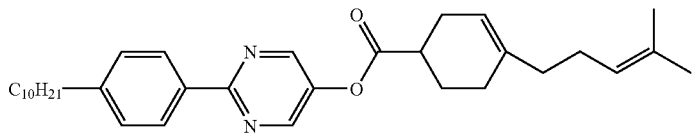
| MDW # | Structure |
|---|---|
| 1701 | 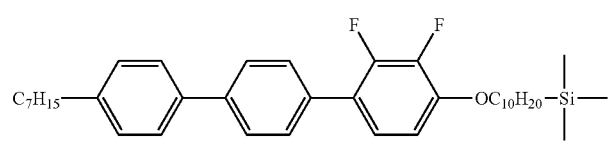 |
| 1669 | 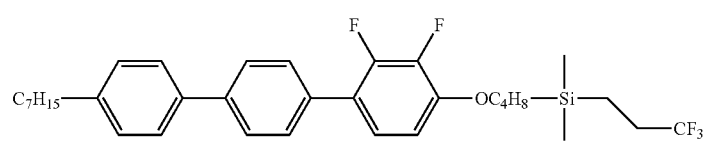 |
| 1658 | 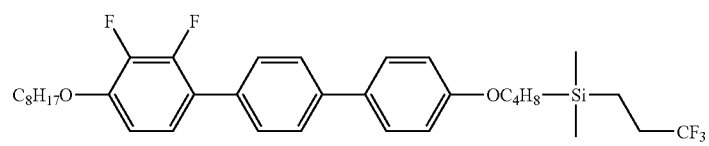 |
| 1592 | 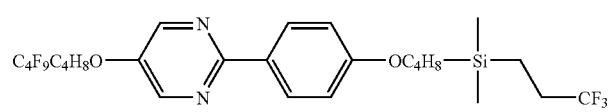 |
| 1532 | 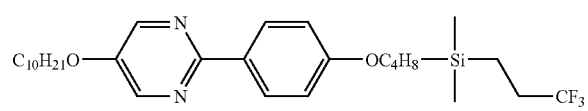 |
| 1632 | 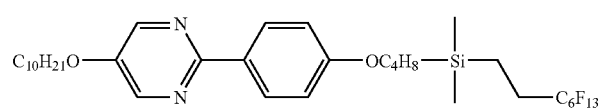 |
| 1586 | 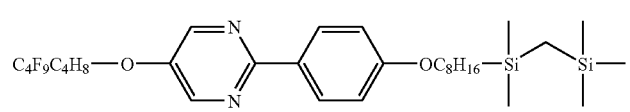 |
| 1709 | 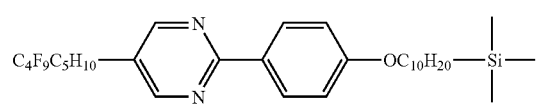 |
| 1597 | 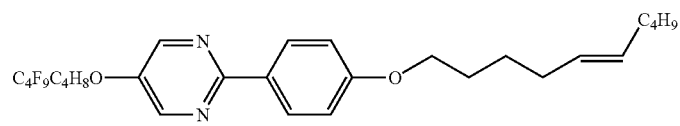 |
MDW 1597
Cr  64.9  SmC  100.4  SmA  102.4  I
    43.3        99.6         101.0

-continued
SCHEME 3
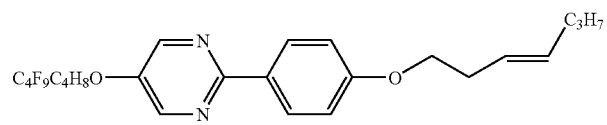
Cr  61.7  SmC  135.0  I
    57.7        134.6
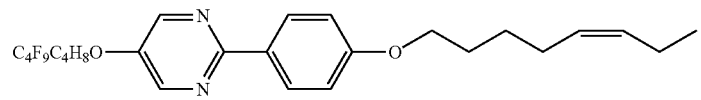
Cr  70.7  SmC  113.8  SmA  115.4  I
    60.7        113.8        114.6
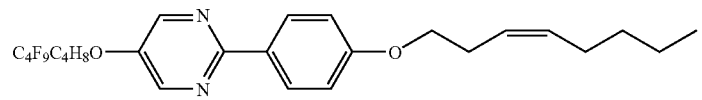
Cr  59.0  SmC  114.2  SmA  121.0  I
1015
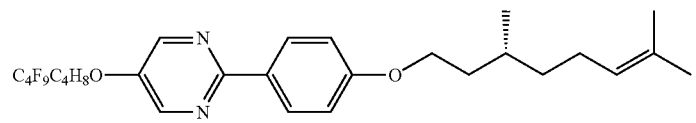
MDW 1015
Cr  62  SmA  67  I
1028
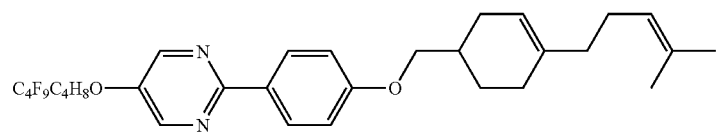
MDW 1028
TABLE 1
| MDW | Structure |
| --- | --- |
| 1342 | 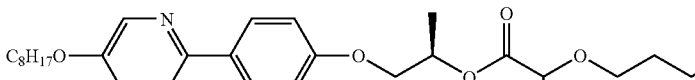 |
| 1341 | 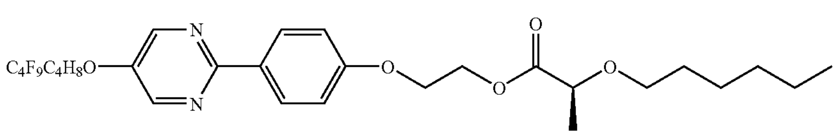 |
| 1369 | 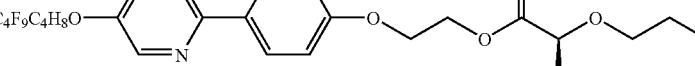 |
| 1368 | 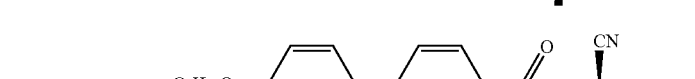 |

TABLE 1-continued
| 1433 | 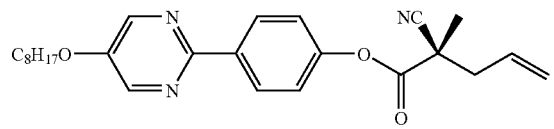 |
| 1432 | 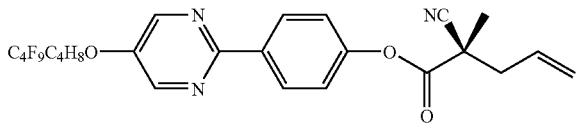 |
| 1276 | 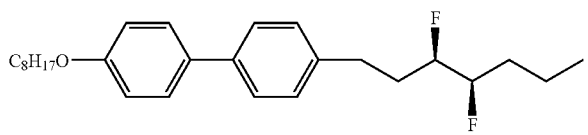 |
| 1415 | 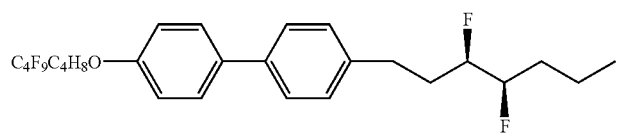 |
| 1392 | 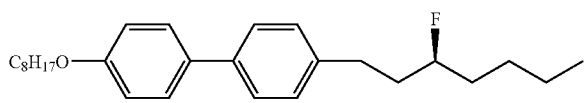 |
| 1393 | 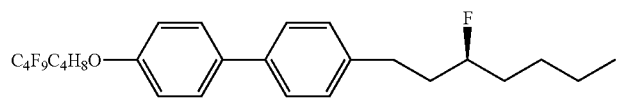 |
| 1473 | 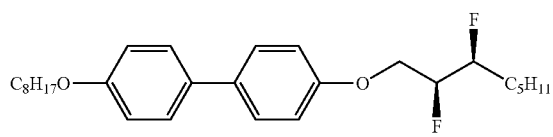 |
| 1474 | 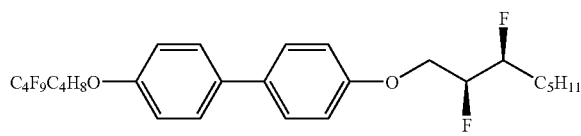 |
| 1471 | 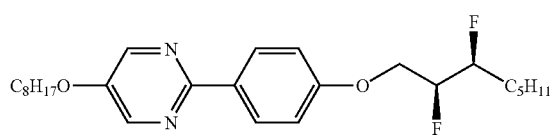 |
| 1470 | 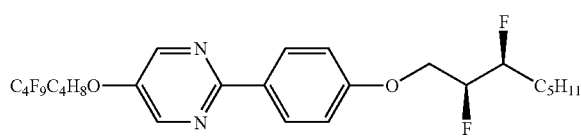 |
| 1450 | 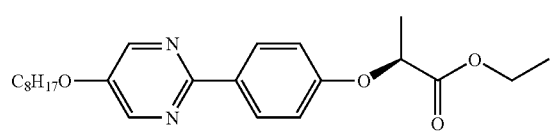 |

TABLE 1-continued

| | |
|---|---|
| 1160 | C₄F₉C₄H₈O—[pyrimidine]—[phenyl]—O—CH(CH₃)—C(=O)—OC₂H₅ |
| 1195 | C₈H₁₇O—[pyrimidine]—[phenyl]—O—CH(CH₃)—C(=O)—OC₄H₈C₄F₉ |
| 1192 | C₄F₉C₄H₈O—[pyrimidine]—[phenyl]—O—CH(CH₃)—C(=O)—OC₄H₈C₄F₉ |
| 1377 | C₈H₁₇O—[pyrimidine]—[phenyl]—O—C(=O)—[2,2-dimethyl-1,3-dioxolan-4-yl] |
| 1175 | C₄F₉C₄H₈O—[pyrimidine]—[phenyl]—O—C(=O)—[2,2-dimethyl-1,3-dioxolan-4-yl] |
| 1400 | C₈H₁₇O—[pyrimidine]—[phenyl]—O—CH₂—[γ-butyrolactone with isobutyl substituent] |
| 1401 | C₄F₉C₄H₈O—[pyrimidine]—[phenyl]—O—CH₂—[γ-butyrolactone with isobutyl substituent] |
| 1426 | C₈H₁₇O—[pyrimidine]—[phenyl]—O—CH₂—[γ-butyrolactone] |
| 1427 | C₄F₉C₄H₈O—[pyrimidine]—[phenyl]—O—CH₂—[γ-butyrolactone] |
| 1153 | C₈H₁₇O—[pyrimidine]—[phenyl]—O—C(=O)—[epoxide]—C₃H₇ |

TABLE 1-continued

| | | Ps | % in |
|---|---|---|---|
| MDW | Phase Diagram | (nC/cm$^2$) | MX6111 |
| 1342 | Cr 41.2 I | 6.3 | 10 |
| 1341 | Cr 98.5 I | 14.5 | 10 |
| 1369 | Cr 95.5 I | 5.0 | 5 |
| 1368 | Cr 126 I | 8.6 | 5 |
| 1433 | Cr 63.3 I | 1.16 | 5 |
| 1432 | Cr 90 I | 2.07 | 5 |
| 1276 | Cr 105.5 I | 3.69 | 5 |
| 1415 | Cr 123 I | 5.18 | 5 |
| 1392 | Cr 71 S$_B$ 92 I | 3.17 | 5 |
| 1393 | I 116 A 94 Sx ? X | 3.84 | 5 |
| 1473 | I 120 X | 6.3 | 5 |
| 1474 | I 137 A 121 X | 7.6 | 5 |
| 1471 | I 93.5 X | 6.1 | 5 |
| 1470 | I 128 A 101.5 X | 7.1 | 5 |
| 1450 | Cr 44 I | 2.99 | 10 |
| 1160 | Cr 89 I | 10.2 | 10 |
| 1195 | Cr 35 I | 0 | 10 |
| 1192 | Cr 86.4 I | 0.8 | 10 |
| 1377 | Cr 114.5 I | 7.25 | 10 |
| 1175 | Cr 124.7 I | 9.9 | 10 |
| 1400 | Cr 134 I | 12.5 | 5 |
| 1401 | Cr 153 I | 13.5 | 5 |
| 1426 | Cr 119 I | 4.59 | 5 |
| 1427 | Cr 150.9 I | 4.89 | 5 |
| 1153 | Cr 75 I | 14.5 | 10 |
| 1159 | Cr 79 I 87 Sx 84 Cr | 41.4 | 10 |
| 1194 | Cr 37 I | 35 | 10 |
| 1252 | Cr 105 I 96 Sx 87 Cr | 25 | 10 |
| 1253 | I 98 S$_A$ 89 Sx$_1$ 85 Sx$_2$ | 17 | 10 |
| 1213 | Cr 79 I 74 Sx 69 Cr | 34.5 | 10 |

DETAILED DESCRIPTION OF THE INVENTION

Synthetic Procedures for High PS Dopant

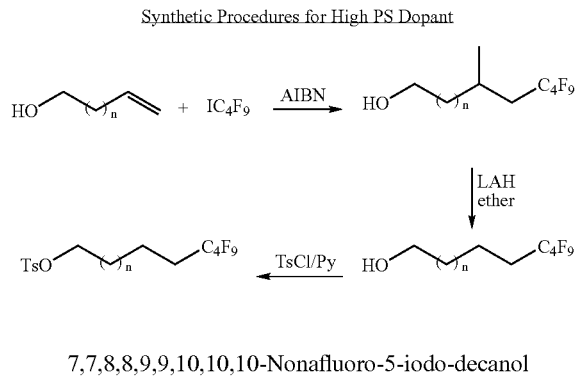

7,7,8,8,9,9,10,10,10-Nonafluoro-5-iodo-decanol

To the mixture of 5 g of 5-hexenol and 17.4 g of perfluoro iodobutane, was added 110 mg of AIBN at RT under $N_2$ atmosphere. After 15 mins, another 110 mg of AIBN was added. The resulting solution was then refluxed at 70° C. for 4 hrs. The reaction mixture was cooled down and used for the next reaction without further purification.

7,7,8,8,9,9,10,10,10-Nonafluoro-decanol

To the solution of 2 g of LAH in 120 ml of abs. ether, was added slowly ca. 22 g of 7,7,8,8,9,9,10,10,10-Nonafluoro-5-iodo-decanol derivative in 30 ml abs. Ether. After addition, the reaction mixture was stirred at RT for two days and then cooled down to 5° C. in the ice water. Water was added slowly until no gas evolved. The solid was filtered through short column of silica gel, washed with ether and ethyl acetate. The filtrate was combined and the solvent was evaporated. The residue was distilled under vacuum to give 13 g (81% yield) of the partial-fluoro alcohol.

7,7,8,8,9,9,10,10,10-Nonafluoro-decyl tosylate

The solution of 9.8 g of partial-fluoro alcohol in 40 ml of pyridine was cooled down to 0° C. in ice-salt water and 6 g of TsCl was added in small portion. After addition the resulting mixture was stirred at 0° C. for two hours and then placed in freezer (−20° C.) for two days. The reaction mixture was poured into ice water and the product was extracted with ethyl acetate twice. The combined organic phase was washed with brine, 10% HCl and again brine three times, and then dried over $MgSO_4$. After evaporation of solvent, pure partial-fluoro tosylate was obtained in yield of 98%.

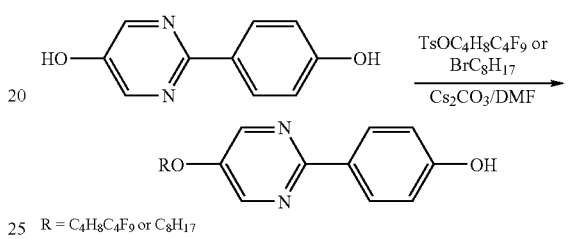

R = $C_4H_8C_4F_9$ or $C_8H_{17}$

4-(2-(5-alkoxypyrimidyl))phenol 25 mmol of alkyltosylate or bromide, 25 mmol of pyrimidylphenol derivative, 30 mmol of $Cs_2CO_3$ and 50 ml of DMF were mixed together and stirred at RT over night. The reaction mixture was then poured into water. The solid was filtered and washed with water. The crude product was dissolved in ethyl acetate, washed with water and dried over $MgSO_4$. After evaporation of solvent, the residue was purified by flash chromatography. The yield is 65%.

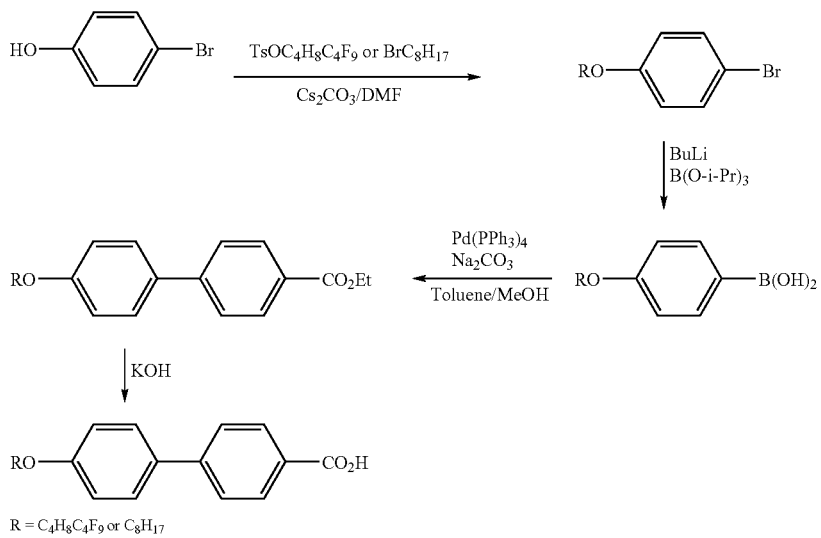

R = $C_4H_8C_4F_9$ or $C_8H_{17}$

4-Alkoxy-1-bromobenzene 25 mmol of tosylate or bromide, 25 mmol of 4-bromophenol, 30 mmol of Cs$_2$CO$_3$ and 50 ml of DMF were mixed together and stirred at RT over night. The reaction mixture was then poured into water and the solid was collected by extraction with ethyl acetate. The organic phase was washed with water and dried over MgSO4. After evaporation of solvent, pure product was obtained in yield of 100%.

4-Alkoxyphenylboronic acid

To the dry flask containing 37 mmol of 4-Alkoxy-1-bromobenzene and 80 ml of THF, cooled to −78° C., 21 ml of BuLi (2.2M in Hexane) was added slowly. After addition the reaction mixture was stirred at −70° C. for 1 Hour and then 17.6 ml of triisopropylborate was added slowly. Reaction solution was allowed to warm up to RT and stirred at RT over night. Then 70 ml of water was added slowly and stirred at RT for two hours. The product was collected by extraction with hexane. The extract was washed with brine and dried over MgSO$_4$. After evaporation of solvent, the residue was purified by short column chromatography to give pure product in yield of 92%.

Ethyl 4-alkoxyphenylbenzoate

To the solution of 1.2 g of ethyl 4-bromobenzoate in 12.5 ml of toluene, was added 6 ml of Na$_2$CO$_3$ (2M aqueous solution), followed by 6 mmol of boronic acid in 3 ml of methanol and 200 mg of Pd(PPh$_3$)$_4$. The resulting mixture was heated up to 80° C. and stirred at this temperature vigorously for 48 hrs. It was then cooled down and partitioned between 30 ml methylene chloride and 25 ml of 2M aqueous Na$_2$CO$_3$. The organic phase was separated, washed with brine and dried over MgSO$_4$. After evaporation of solvent, the residue was purified by flash chromatography. The yield is 86%.

4-alkoxyphenylbenzoic acid is prepared by conventional methods as illustrated above. 2.2 mmol of benzoate derivative, 3 g of KOH and 60 MeOH were stirred at 70° C. over night. Then MeOH was removed and the residue is mixed with water and neutralized with conc.HCl. The solid was collected, washed with water and dried under vacuum. The yield is 95%.

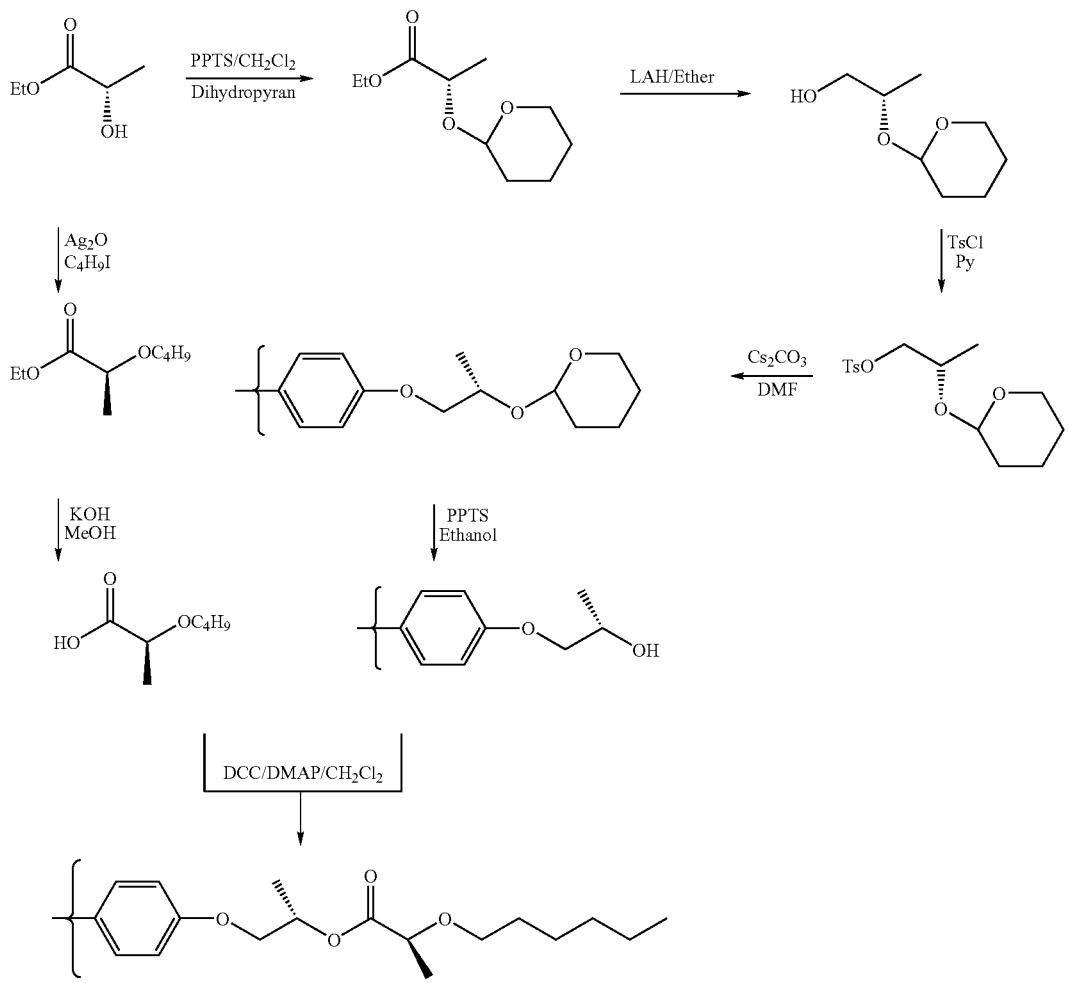

Ethyl [S]-tetrahydropyranyloxy propionate 10 g of L-ethyl lactate, 8.5 g of 3,4-dihydro-2H-pyran, 0.5 g PPTS and 150 ml of methylene chloride were put together and stirred at RT for two days. The excess solvent was removed and the residue was mixed with 80/20 hexane and ethyl acetate. The solid was filtered and the solution was concentrated. The residue was further purified by flash chromatography to give pure product. The yield was 88%.

[S]-2-tetrahydropyranyloxy-1-propanol 4.1 g of THP protected lactate in 80 ml of dry ether was added to a mixture of 2 g of LiAlH4 in 120 ml of dry ether. The addition was controlled to keep a gentle reflux. After addition, the reaction mixture was stirred at RT for 3 hrs and 10 ml of water was added with great care. The mixture was then filtered through a short column of silica gel and washed with ether. The solvent was evaporated to give pure product (yield~100%).

[S]-2-tetrahydropyranyloxy-1-propyltosylation

The solution of 3.2 g of [S]-2-tetrahydropyranyloxy-1-propanol in 30 ml of pyridine was cooled down to 0° C. in ice-salt water and 3.5 g of TsCl was added in small portion. After addition the resulting mixture was stirred at 0° C. for two hours and then placed in freezer (−20° C.) for two days. The reaction mixture was poured into ice water and the product was extracted with ethyl acetate twice. The organic phase was washed with brine, 10% HCl, diluted $Na_2CO_3$ and dried over MgSO4. After evaporation of solvent, the residue was purified by flash chromatography to give 6 g of tosylate (yield 95%).

[S]-2-tetrahydropyranyloxy-1-propoxyphenyl derivative 2.1 mmol of Tosylate, 2 mmol of phenol, 2 mmol of $CS_2CO_3$ and 20 ml of DMF were put together and stirred at RT over night. Then the reaction mixture was poured into water and the product was collected by extraction. The organic solution was washed with brine and dried over $MgSO_4$. After evaporation of solvent, the residue was purified by flash chromatography to give pure product with yield of over 95%.

[S]-2-hydroxy-1-propoxyphenyl derivative 0.6 g of [S]-2-tetrahydropyranyloxy-1-propoxyphenyl derivative, 0.1 g of PPTS and 20 ml of ethanol were stirred at 95° C. for 3 hrs and then the ethanol was removed. The residue was mixed with ethyl acetate and filtered through short column silica gel, washed with ethyl acetate. The combined filtrate was evaporated to dryness to give pure product (yield 82%).

Ethyl [S]-2-methyl-3-oxo-heptanoate 1.5 g of L-ethyl lactate, 4.5 g of Ag2O and 15 ml of iodobutane were mixed together and stirred at 40° over night. The black solid was filtered out and the filtrate was distilled to give 1.4 g of product (yield 65%).

[S]-2-methyl-3-oxo-heptanoic acid 1 g of Ethyl [S]-2-methyl-3-oxo-heptanoate, 0.5 g of KOH and 15 MeOH were stirred at 50° C. for 4 hrs. Then MeOH was removed and the residue is mixed with water, neutralized with conc.HCl and extracted with methylene chloride. The combined organic phase was washed with water for 3–4 times and dried over $MgSO_4$. After evaporation of solvent, 0.8 g of product was obtained (yield 95%).

[S,S]-1-Phenoxy-2-propyl 2-methyl-3-oxo-heptanoate derivative 80 mg of [S]-2-methyl-3-oxo-heptanoic acid, 150 mg of [S]-2-hydroxy-1-propoxyphenyl derivative, 160 mg of DCC, 10 mg of DMAP and 20 ml of methylene chloride were put together and stirred at RT over night. The solid was filtered out and the filtrate was concentrated. The residue was purified by flash chromatography to give pure product with yield over 80%.

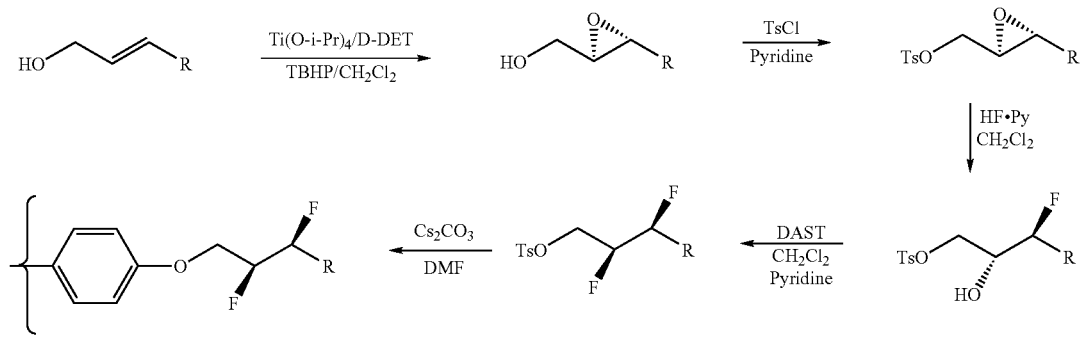

(2S, cis)-3-propyloxiranemethanol

To the mixture of 210 ml methylene chloride and 4 g of activated 4 Å powder sieves, cooled to −20° C., 1.5 g of L-(+) diethyl tartrate and 1.5 g of Ti(O—i—Pr)$_4$ was added with stirring. Then 20 ml of TBHP in methylene chloride (ca. 5–6 M) was added through addition funnel at a moderate rate (ca. 5 minutes). The resulting mixture was stirred at −20° C. for 30 minutes and 5 g of cis-3-hexene-1-ol in 25 ml of methylene chloride was added dropwise over period of 20 mins. The temperature was kept between −15 to −20° C. The stirring was continued for another hour and then stored in freezer (−20° C.) for two days. After warmed up to 0° C., 30 ml of water was added and the mixture is stirred for 1 hour, while allowing it to warm up to RT. 6 ml of 30% aqueous solution of NaOH saturated with NaCl was added and stirred vigorously. After 20 mins, there was a phase separation. The bottom organic phase was removed and top aqueous phase was extracted with methylene chloride. The combined organic phase was then dried and the solvent was removed. The residue is further purified by distillation to give pure product with yield of 75%.

(2S, cis)-3-propyloxiranemethyl tosylate

The solution of 1 g of (2S, cis)-3-propyloxiranemethanol in 10 ml of pyridine was cooled down to 0° C. in ice-salt water and 4.5 g of TsCl was added in small portion. After addition the resulting mixture was stirred at 0° C. for one hours and then placed in refrigerator (5° C.) for three days. The reaction mixture was poured into ice water and the product was extracted with ether. The combined organic phase was washed with 15% HCl cold solution, saturated NaHCO$_3$ and brine, and dried over MgSO4. After evaporation of solvent, the residue was further purified by flash chromatography to give 2.4 g of tosylate (yield 97%).

(2S, 3R)-3-fluoro-2-hydroxyhexyl tosylate

To the solution of 18.5 mmol of tosylate in 180 ml methylene chloride, cooled in dry ice-acetone, was added 5.7 ml of HF/Py. After addition the reaction solution was allowed to warm up slowly to −50° C. (it took about 2 hrs) and placed in freezer (−25° C.) over night. Then it was poured into water. Separated the organic phase, followed by washed with NaHCO3 and water. Dried over MgSO4. After evaporation of solvent, an oil product was obtained, which was used directly for the next reaction (yield 110%).

(2R, 3R)-2,3-difluorohexyl tosylate

To the solution of 0.71 mmol of monohydroxy derivative in 30 ml of methylene chloride, cooled down to −78° C., was added 0.4 ml of DAST. After addition, the reaction solution was allowed to warm up to RT slowly and stirred at RT over night. Then it was poured into water, extracted with ethyl acetate, washed with brine and dried over MgSO$_4$. After evaporation of solvent, the residue was purified by flash chromatography. Yield is 50%.

(2R, 3R)-2,3-difluorohexylox phenyl derivative 2.1 mmol of Tosylate, 2 mmol of phenol, 2 mmol of Cs$_2$CO$_3$ and 20 ml of DMF were put together and stirred at RT over night. Then the reaction mixture was poured into water and the product was collected by extraction. The organic solution was washed with brine and dried over MgSO$_4$. After evaporation of solvent, the residue was purified by flash chromatography to give pure product with yield over 95%.

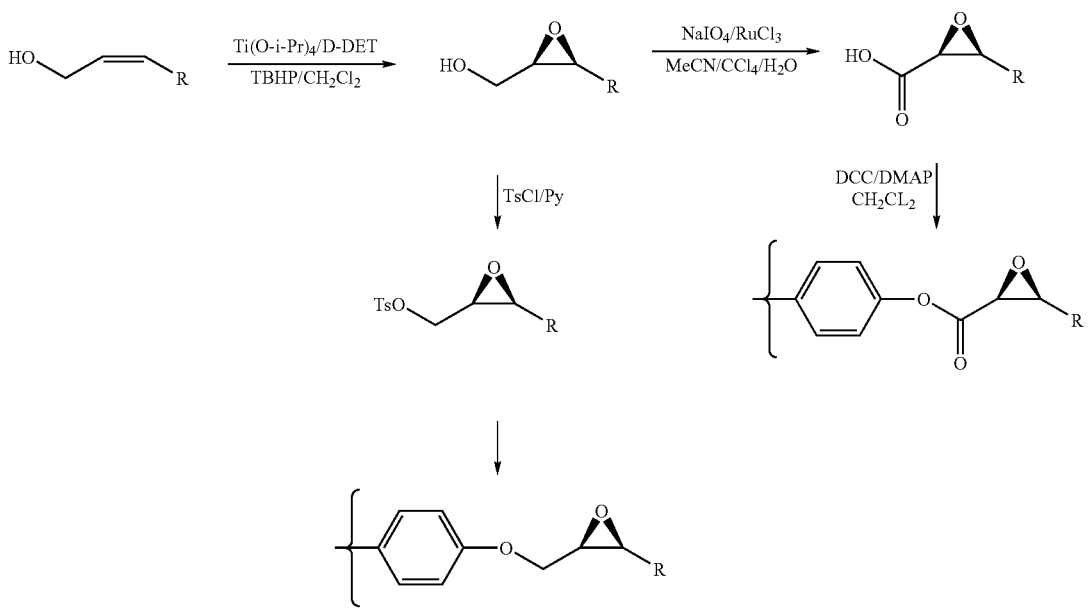

(2S, cis)-3-propyloxiranemethanol

To the mixture of 210 ml methylene chloride and 4 g of activated 4 Å powder sieves, cooled to −20° C., 1.5 g of L-(+) diethyl tartrate and 1.5 g of Ti(O—i—Pr)$_4$ was added with stirring. Then 20 ml of TBHP in methylene chloride (ca. 5–6 M) was added through addition funnel at a moderate rate (ca. 5 minutes). The resulting mixture was stirred at −20° C. for 30 minutes and 5 g of cis-3-hexene-1-ol in 25 ml of methylene chloride was added dropwise over period of 20 mins. The temperature was kept between −15 to −20° C. The stirring was continued for another hour and then stored in freezer (−20° C.) for two days. After warmed up to 0° C., 30 ml of water was added and the mixture is stirred for 1 hour, while allowing it to warm up to RT. 6 ml of 30% aqueous solution of NaOH saturated with NaCl was added and stirred vigorously. After 20 mins, there was a phase separation. The bottom organic phase was removed and top aqueous phase was extracted with methylene chloride. The combined organic phase was then dried and the solvent was removed. The residue is further purified by distillation to give pure product with yield of 75%.

(2S, cis)-3-propyloxiranecarboxylic acid

A flask was charged with 34 ml of CCl$_4$, 34 ml of acetonitrle and 2 g of (2S, cis)-3-propyloxiranemethanol.

Then 11 g of NaIO4 in 51 ml of water were added, followed by 86 mg of RuCl3 to this biphasic solution. The mixture was stirred vigorously for 3 hrs at RT and 100 ml of methylene chloride was added. The organic phase was separated and water phase was extracted with methylene chloride. The combined black organic phase was dried over MgSO$_4$ and concentrated. The residue was diluted with ether and filtered through celite to give colorless solution. After evaporation of solvent a pure product was obtained (yield 67%).

(2S, cis)-3-propyloxiranemethoxy phenyl derivative 2.1 mmol of Tosylate, 2 mmol of phenol, 2 mmol of Cs$_2$CO$_3$ and 20 ml of DMF were put together and stirred at RT over night. Then the reaction mixture was poured into water and the product was collected by extraction. The organic solution was washed with brine and dried over MgSO$_4$. After evaporation of solvent, the residue was purified by flash chromatography to give pure product with yield over 95%.

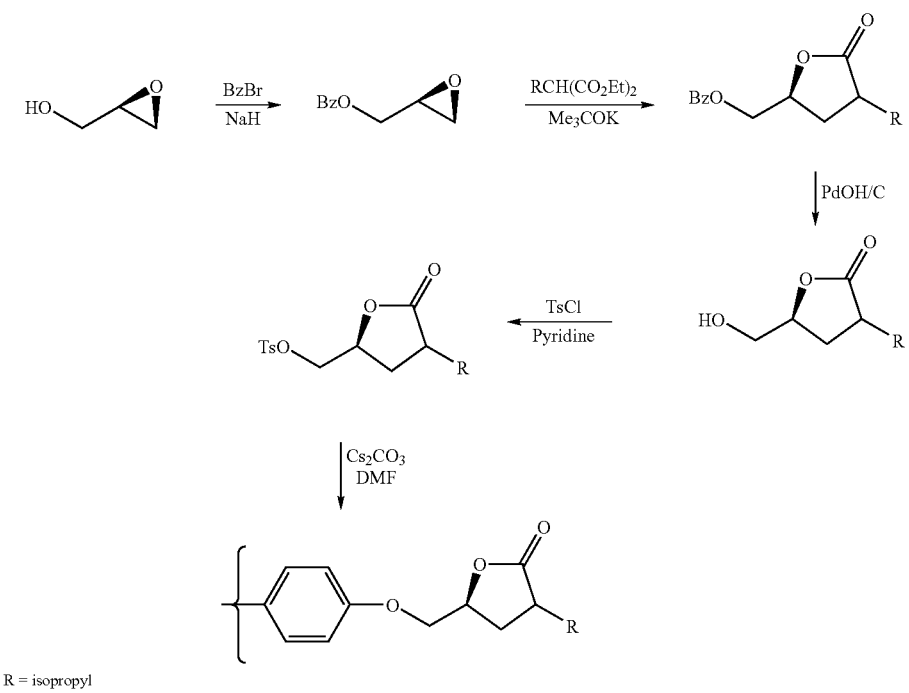

R = isopropyl (2S, cis)-3-propyloxiranemethyl tosylate

The solution of 1 g of (2S, cis)-3-propyloxiranemethanol in 10 ml of pyridine was cooled down to 0° C. in ice-salt water and 4.5 g of TsCl was added in small portion. After addition the resulting mixture was stirred at 0° C. for one hours and then placed in refrigerator (5° C.) for three days. The reaction mixture was poured into ice water and the product was extracted with ether. The combined organic phase was washed with 15% HCl cold solution, saturated NaHCO$_3$ and brine, and dried over MgSO4. After evaporation of solvent, the residue was further purified by flash chromatography to give 2.4 g of tosylate (yield 97%).

Phenyl (2S, cis)-3-propyloxiranecarboxylate derivative 200 mg of (2S, cis)-3-propyloxiranecarboxylic acid, 0.9 equivalent of phenol derivatives, 300 mg of DCC, 15 mg of DMAP and 20 ml of methylene chloride were put together and stirred at RT over night. The solid was filtered out and the filtrate was concentrated. The residue was purified by flash chromatography to give pure product with yield over 80%.

[R]-3-Benzyloxy propylene oxide

To the mixture of 1.65 g of NaH in 150 ml of THF, 5 g of [R]-glycidol in 5 ml of THF was added. After stirring at RT for 10 mins, 12 g of benzyl bromide was added and the resulting mixture was stirred at RT for 3 hours. It was then hydrolyzed carefully with water and most of THF was removed. The rest was mixed with water and extracted with ethyl acetate. The organic solution was washed with brine and dried over MgSO4. After evaporation of solvent the residue was purified by flash chromatography. Yield is 54%

[R]-5-benzyloxymethyl-3-isobutyl-2(5H)-furanone

To the solution of 11 g of potassium t-butoxide in 60 ml of t-butanol, was added 2 g of [R]-3-Benzyloxy propylene oxide, followed by 20 g of diethyl isobutyl malonate. The resulting mixture was refluxed for 15 hrs. The t-butanol was removed by distillation and the residue was poured into water. The crude product was collected by extraction with ethyl acetate. The organic phase was washed with brine and dried over MgSO4. After evaporation of solvent, the residue was distillated to remove excess diethyl isobutyl malonate and the rest was further purified by flash chromatography. Yield is 72%.

[R]-5-hydroxymethyl-3-isobutyl-2(5H)-furanone 2.3 g of [R]-5-benzyloxymethyl-3-isobutyl-2(5H)-furanone, 150 mg of PdOH/C in 50 ml of ethanol was stirred at RT over night under H$_2$ atmosphere. Then the catalyst was filtered out and filtrate was evaporated to dryness to give the pure compound in yield of 99%.

[R]-5-Tosylmethyl-3-isobutyl-2(5H)-furanone

The solution of 1.5 g of [R]-5-hydroxymethyl-3-isobutyl-2(5H)-furanone in 10 ml of pyridine was cooled down to 0° C. in ice-salt water and 1.7 g of TsCl was added in small portion. After addition the resulting mixture was stirred at 0° C. for two hours and then placed in freezer (−20° C.) for two days. The reaction mixture was poured into ice water and the product was extracted with ethyl acetate twice. The organic phase was washed with brine, 10% HCl, diluted Na$_2$CO$_3$ and dried over MgSO4. After evaporation of solvent, the residue was purified by flash chromatography to give 6 g of tosylate (yield 95%).

[R]-5-phenoxymethyl-3-isobutyl-2(5H)-furanone derivative 2.1 mmol of [R]-5-Tosylmethyl-3-isobutyl-2(5H)-furanone, 2 mmol of phenol derivative, 2 mmol of Cs$_2$CO$_3$ and 20 ml of DMF were put together and stirred at RT over night. Then the reaction mixture was poured into water and the product was collected by extraction. The organic solution was washed with brine and dried over MgSO$_4$. After evaporation of solvent, the residue was purified by flash chromatography to give pure product with yield over 95%.

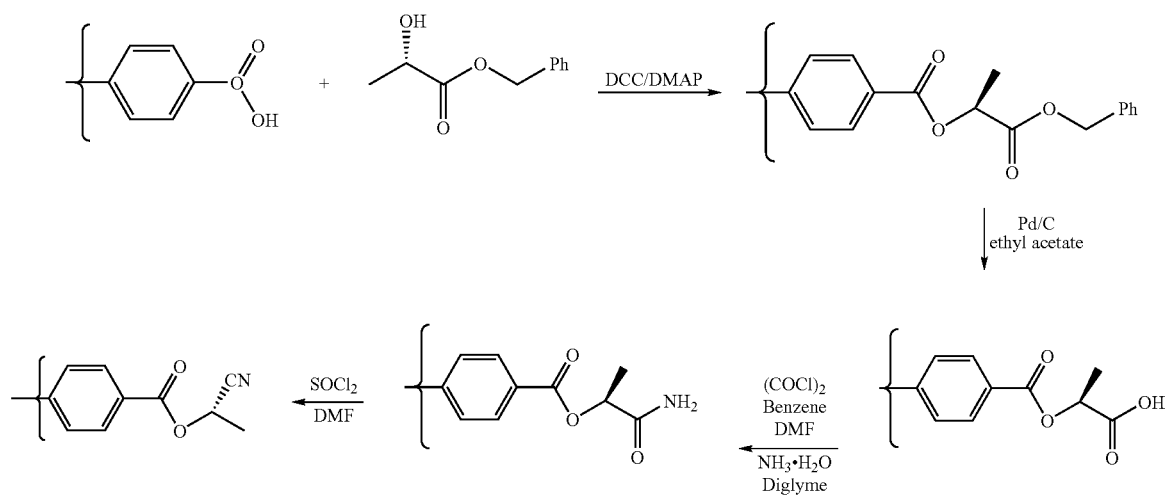

Synthetic scheme for three-ring compounds

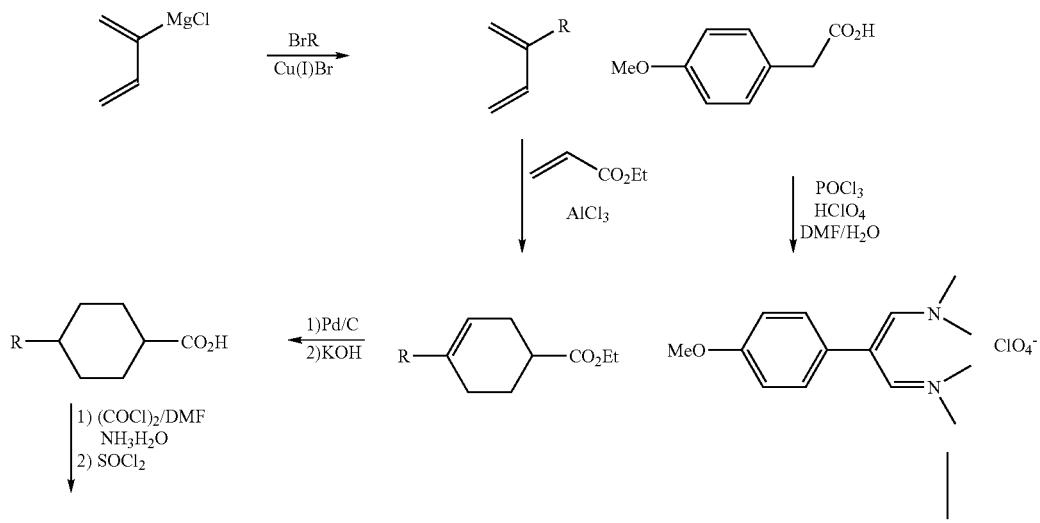

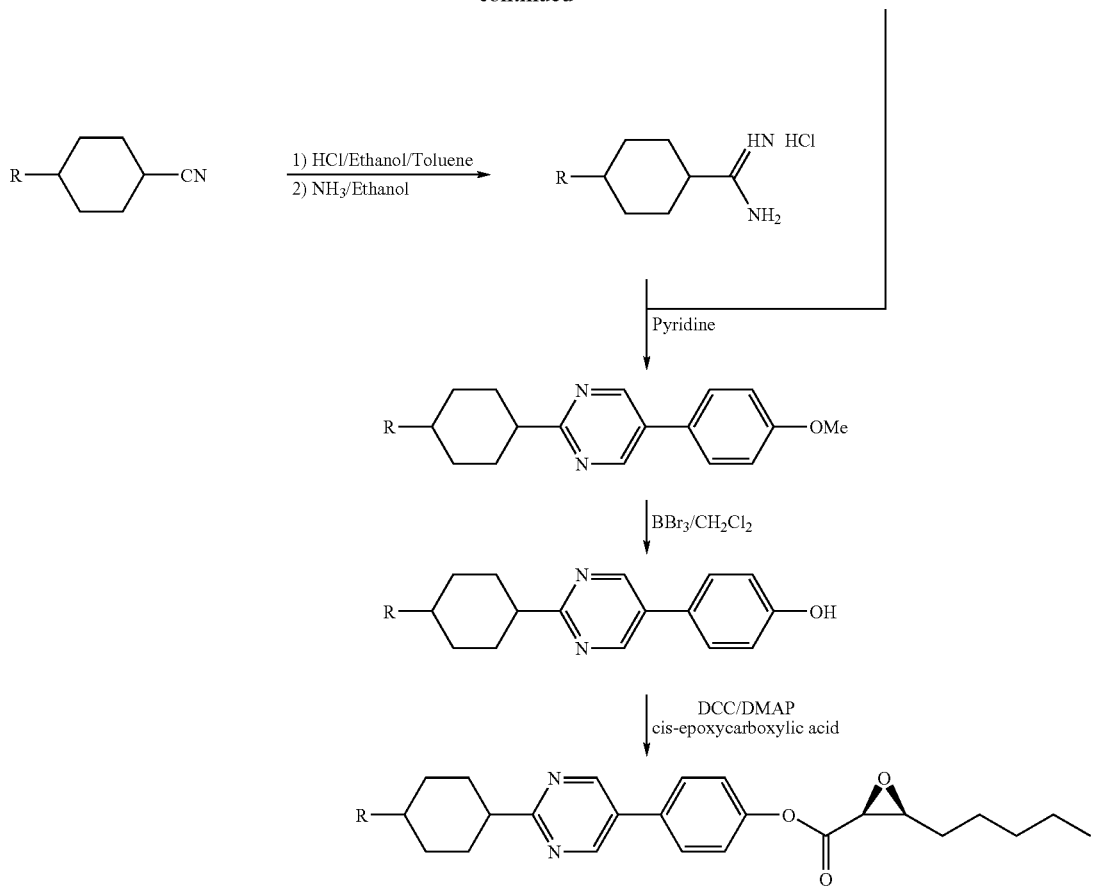
R = C$_4$H$_8$C$_4$F$_9$ or C$_8$H$_{17}$
TABLE 2
Composition of MX 6111
| MX 6111 Structure and MDW # | % Composition |
|---|---|
| MDW 1 — C$_7$H$_{15}$–[pyrimidine]–[phenyl]–OC$_6$H$_{13}$ | 5.6 |
| MDW 2 — C$_9$H$_{19}$–[pyrimidine]–[phenyl]–OC$_7$H$_{15}$ | 5.6 |
| MDW 3 — C$_7$H$_{15}$–[pyrimidine]–[phenyl]–OC$_8$H$_{17}$ | 5.6 |
| MDW 4 — C$_9$H$_{19}$–[pyrimidine]–[phenyl]–OC$_8$H$_{17}$ | 7.2 |

TABLE 2-continued

Composition of MX 6111

| MX 6111 Structure and MDW # | % Composition |
|---|---|
| MDW 22 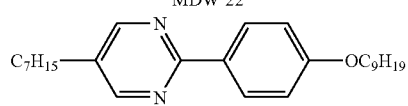 | 5.6 |
| MDW 31 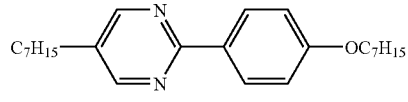 | 5.6 |
| MDW 343 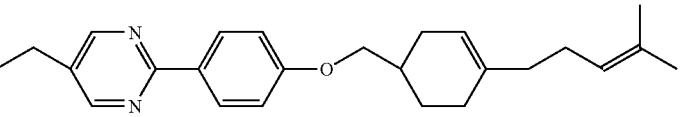 | 20 |
| MDW 764 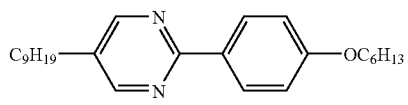 | 9.6 |
| MDW 1287 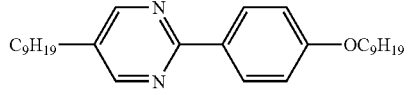 | 33.6 |

We claim:

1. A chiral, non-racemic liquid crystal composition comprising a chiral compound of the formula:

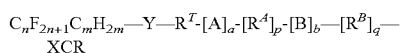

wherein
- n is an integer from 1 to 20;
- m is an integer from 2 to 20;
- a, b, p and q are either 0 or 1, when p is 0, a is 0 and when q is 0, b is 0;
- Y is a single bond or oxygen;
- X is selected from the group consisting of a single bond, oxygen, —CO—, —O—CO—, —CO—O— and a lower alkylene group where one or more carbon atoms is optionally substituted with one or more of oxygen or —CO—;
- CR is selected from the group consisting of:

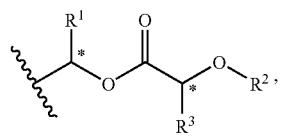 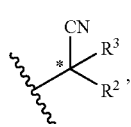

-continued

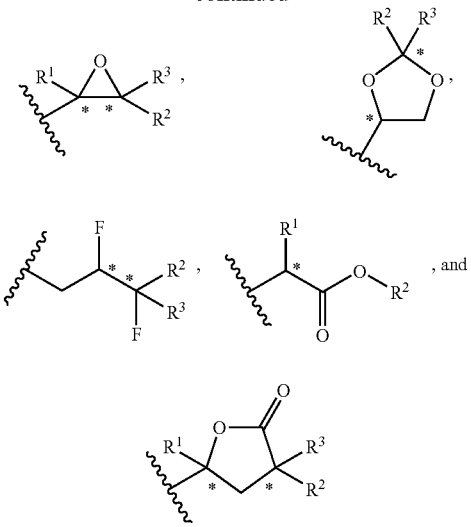

wherein
each of $R^1$ and $R^3$ is independently hydrogen, lower alkyl, lower alkenyl, lower haloalkyl, or lower haloalkenyl;
$R^2$ is an alkyl, alkenyl, ether, thioether, or silyl group having from 1 to about 20 carbon atoms wherein one or more $CH_2$ groups are optionally replaced with —S—, —O—, —CO—, —CO—O—, —O—CO—, or —Si(R')$_2$, and where R' is lower alkyl or lower haloalkyl, provided at least one carbon center indicated by * is an asymmetric carbon center;

A and B, independently, are linker groups selected from the group consisting of —CO—, —O—CO—, —CO—O—, —CH$_2$—CH$_2$—, —CH$_2$—CH$_2$—O—, —O—CH$_2$—CH$_2$—, —C≡C—, —CH=CH—, and —CH=CH—CH=CH—, and $R^T$, $R^A$, and $R^B$ together represent a mesogenic core, wherein each of the $R^T$, $R^A$, and $R^B$ is independently selected from the group consisting of cycloalkylene, and heterocycloalkylene, cycloalkylene, heterocycloalkenylene, arylene, and heteroarylene each of which is independently optionally substituted with one or more substituents selected from the group consisting of halide, alkyl, haloalkyl, alkenyl, haloalkenyl, nitro, and nitrile.

2. The composition of claim 1 wherein CR is selected from the group consisting:

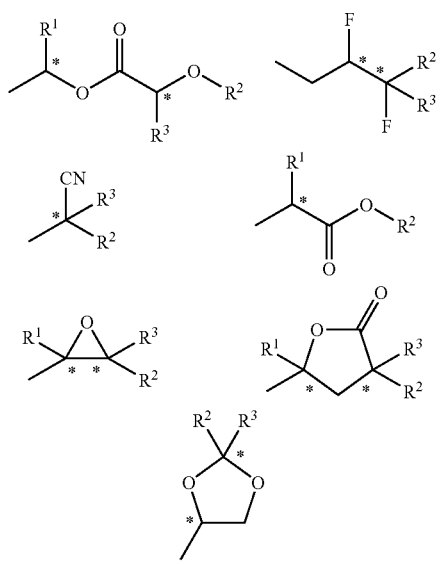

each $R^T$, $R^A$, and $R^B$ is independently selected from the group consisting of naphthylene, cyclohexylene, 6-membered heterocycloalkylene comprising one or two ring nitrogen atoms, cyclohexenylene, 6-membered heterocycloalkenylene comprising one or two ring nitrogen atoms, phenylene, and heteroarylene comprising one or two ring nitrogen atoms each of which is independently optionally substituted with one or more substituents selected from the group consisting of halide, alkyl, haloalkyl, alkenyl, haloalkenyl, nitro, and nitrile.

3. The composition of claim 1 wherein each of $R^T$, $R^A$, and $R^B$ is independently selected from the group consisting of naphthylene, phenylene, cyclohexylene, cyclohexenylene, pyrimidinylene, pyridinylene, 1,2,34-tetrahydronaphthylene, and 1,4-dihydronaphthylene.

4. The composition of claim 1, wherein said mesogenic core is a biaryl moiety.

5. The composition of claim 1 wherein said mesogenic core selected from the group consisting of:

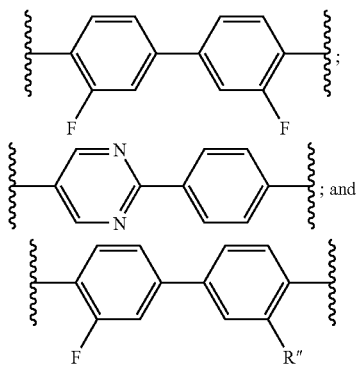

where R" is lower alkyl.

6. The composition of claim 1, wherein said chiral, non-racemic liquid crystal composition further comprises an achiral liquid crystal host.

7. The composition of claim 6, wherein the said achiral liquid crystal host comprises an achiral compound selected from the group consisting of:

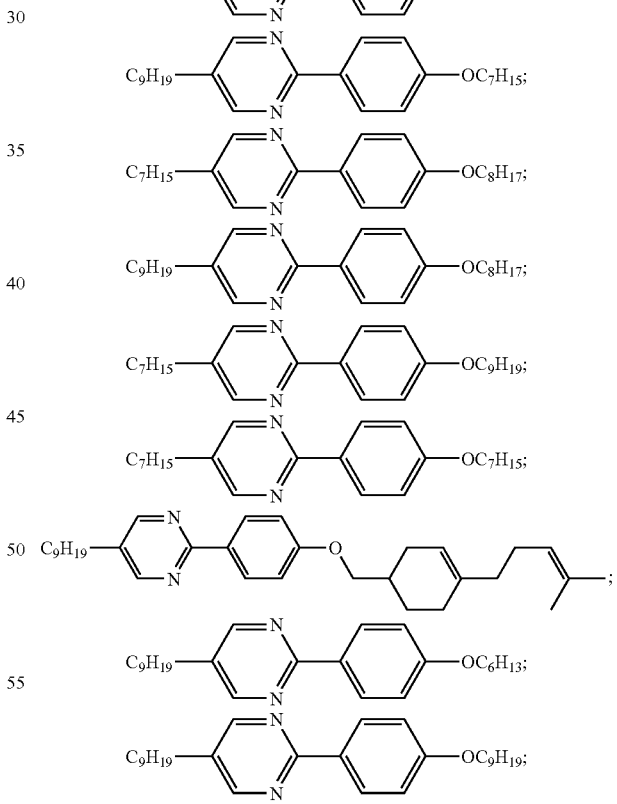

and a mixture of two or more thereof.

8. The composition of claim 1 wherein n=m.

9. The composition of claim 1 wherein Y is O.

10. The composition of claim 1 wherein the total amount of chiral compound in said chiral, non-racemic liquid crystal composition is 10% or less.

11. The composition of claim 1 which has Ps of 10 nC/cm² or more at room temperature.

12. The composition of claim 11 wherein the total amount of chiral compound in said chiral, non-racemic liquid crystal composition is 5% by weight or less.

13. A compound having the formula:

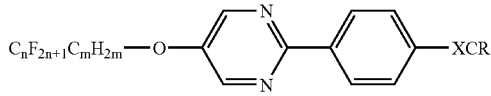

wherein
n and m are integers ranging from 1 to about 20;
X is selected from the group consisting of a single bond, oxygen, —CO—, —OCO—, —CO—O—, and a lower alkyl group, wherein one or more carbon atoms of said lower alkyl group is optionally replaced with oxygen or —CO—; and
CR is selected from the group consisting of:

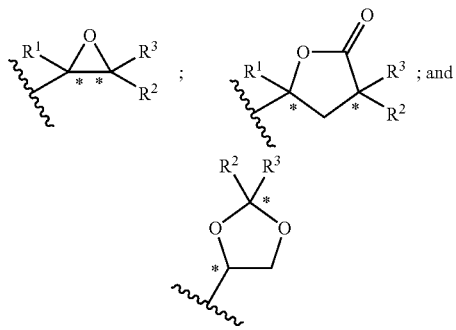

wherein
R¹ and R³, independently of each other, are hydrogen, lower alkyl, lower alkenyl, lower haloalkyl, or lower haloalkenyl; and
R² is hydrogen, alkyl, alkenyl, ether, thioether, or silyl group having from 1 to about 20 carbon atoms wherein one or more CH₂ groups are optionally replaced with —S—, —O—, —CO—, —CO—O—, —O—CO—, or —Si(R')₂—, wherein R' is a lower alkyl optionally substituted with one or more halogens;
provided at least one carbon center indicated by * is an asymmetric carbon center.

14. A chiral, non-racemic liquid crystal composition comprising a chiral compound of the formula:

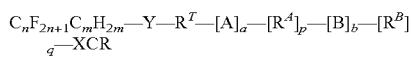

wherein
n is an integer from 1 to 20;
m is an integer from 2 to 20;
a, b, p and q are either 0 or 1, when p is 0, a is 0 and when q is 0, b is 0;
Y is a singe bond or an oxygen;
X is selected from the group consisting of a single bond, oxygen, —CO—, —O—CO—, —CO—O— and a lower alkyl group where one or more carbon atoms is optionally substituted with one or more of oxygen or —CO—;

CR is selected from the group consisting of:

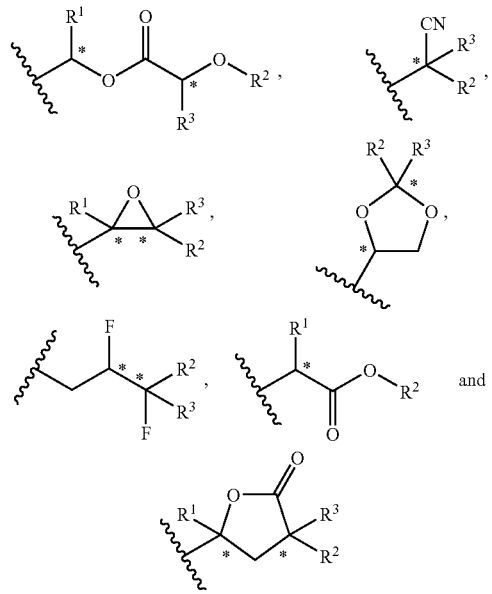

wherein
each of R¹ and R³ is independently hydrogen, lower alkyl, lower alkenyl, lower haloalkyl, or lower haloalkenyl;
R² is an alkyl, alkenyl, ether, thioether, or silyl group having from 1 to about 20 carbon atoms wherein one or more CH₂ groups are optionally replaced with —S—, —O—, —CO—, —CO—O—, —O—CO—, or —Si(R')₂, and where R' is lower alkyl lower haloalkyl,
provided at least one carbon center indicated by * is an asymmetric carbon center;
A and B, independently, are linker groups selected from the group consisting of —CO—, —O—CO—, —CO—O—, —CH₂—CH₂—, —CH₂—CH₂—O—, —O—CH₂—CH₂—, —C≡C—, —CH=CH—, and —CH=CH—CH=CH—; and
$R^T$, $R^A$, and $R^B$ together represent a mesogenic core, wherein each of $R^T$, $R^A$, and $R^B$ is independently selected from the group consisting of:
(a) cyclohexylene,
(b) 6-membered heterocycloalkylene comprising one or two heteroatoms each of which is independently selected from the group consisting of nitrogen and oxygen,
(c) cycloalkenylene,
(d) 6-membered heterocycloalkenylene comprising one or two heteroatoms each of which is independently selected from the group consisting of nitrogen and oxygen,
(e) phenylene,
(f) naphthylene, and
(g) heteroarylene comprising one or two heteroatoms each of which is independently selected from the group consisting of nitrogen and oxygen,
wherein each of $R^T$, $R^A$, and $R^B$ is independently optionally substituted with one or more substituents selected from the group consisting of halide, alkyl, haloalkyl, alkenyl, haloalkenyl, nitro, and nitrile.

15. A chiral, non-racemic liquid crystal composition which comprises one or more chiral compounds of claim 13.

16. A compound of the formula:

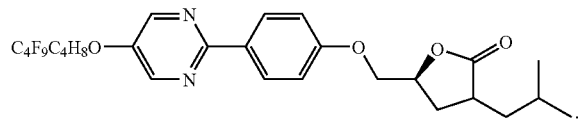

17. The chiral, non-racemic liquid crystal composition of claim 14, wherein the chiral compound is the formula:

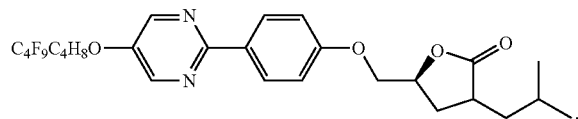

18. A non-racemic liquid crystal composition comprising a rod-like chiral liquid crystal compound and optionally an achiral liquid crystal host, wherein said rod-like chiral liquid crystal compound comprises a mesogenic core moiety having an achiral fluorinated alkyl tail on one end of the long axis of said mesogenic core moiety and a chiral tail on the other end of the long axis of said mesogenic core moiety, wherein:

said mesogenic core comprises a cyclic ring system, wherein said cyclic ring system is selected from the group consisting of cycloalkylene, cycloalkenylene, heterocycloalkylene, heterocycloalkenylene, arylene, heteroarylene, and a combination of two or more thereof; and said chiral tail comprises a chiral moiety selected from the group consisting of:

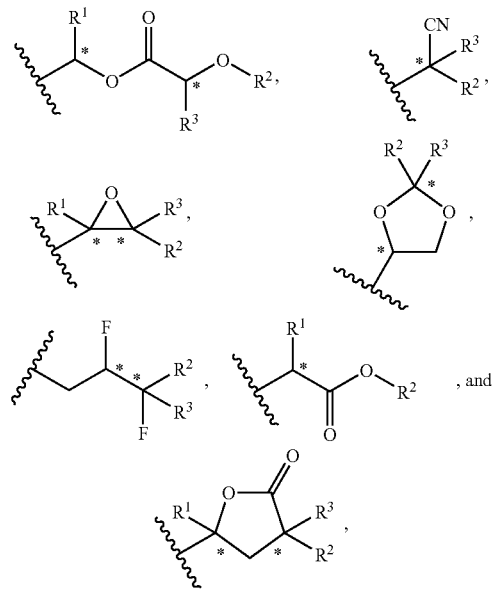

wherein
each of $R^1$ and $R^3$ is independently hydrogen, lower alkyl, lower alkenyl, lower haloalkyl, or lower haloalkenyl; and $R^2$ is an alkyl, alkenyl, ether, thioether, or silyl group having from 1 to about 20 carbon atoms wherein one or more CH$_2$ groups are optionally replaced with —S—, —O—, —CO—, —CO—O—, —O—CO—, or —Si(R')$_2$, and where R' is lower alkyl or lower haloalkyl;

provided at least one carbon center indicated by * is an asymmetric carbon center.

19. The non-racemic liquid crystal composition of claim 18, wherein said mesogenic core moiety comprises three cyclic ring systems or less.

20. The non-racemic liquid crystal composition of claim 19, wherein each of said cyclic ring system is selected from the group consisting of cyclohexylene, cyclohexenylene, heterocycloalkylene comprising one or two ring nitrogen atoms, heterocycloalkenylene comprising one or two ring nitrogen atoms, phenylene, naphthylene, an heteroarylene comprising one or two ring nitrogen atoms.

21. The non-racemic liquid crystal composition of claim 18, wherein each of said cyclic ring system is independently a six-membered monocyclic ring system or a ten-membered bicyclic ring system.

22. A rod-like liquid crystal compound comprising mesogenic core moiety, wherein said mesogenic core moiety is substituted with an achiral fluorinated alkyl substituent on one end of the long axis of said mesogenic core moiety and a chiral substituent on the other end of the long axis of said mesogenic core moiety, wherein:

said mesogenic core comprises a cyclic ring system, wherein said cyclic ring system is selected from the group consisting of cycloalkylene, cycloalkenylene, heterocycloalkylene, heterocycloalkenylene, arylene, heteroarylene, and a combination of two or more thereof, and said chiral substituent comprises a chiral moiety selected from the group consisting of:

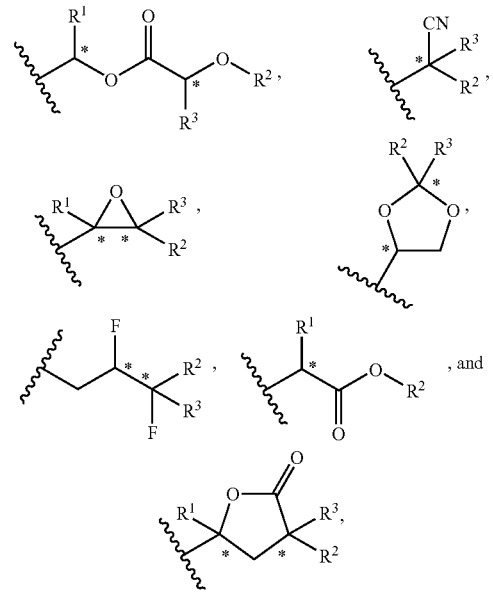

wherein
- each of $R^1$ and $R^3$ is independently hydrogen, lower alkyl, lower alkenyl, lower haloalkyl, or lower haloalkenyl; and
- $R^2$ is an alkyl, alkenyl, ether, thioether, or silyl group having from 1 to about 20 carbon atoms wherein one or more $CH_2$ groups are optionally replaced with —S—, —O—, —CO—, —CO—O—, O—CO—, or —Si(R')$_2$, and where R' is lower alkyl or lower haloalkyl;
- provided at least one carbon center indicated by * is an asymmetric carbon center.

* * * * *